United States Patent
Smith et al.

(10) Patent No.: US 11,860,163 B2
(45) Date of Patent: Jan. 2, 2024

(54) METHODS AND COMPOSITIONS FOR IDENTIFYING AND TREATING SUBJECTS AT RISK FOR POOR CAR T CELL THERAPY RESPONSE

(71) Applicant: MEMORIAL SLOAN-KETTERING CANCER CENTER, New York, NY (US)

(72) Inventors: Melody Smith, New York, NY (US); Marcel van den Brink, New York, NY (US); Eric Pamer, Montclair, NJ (US); Eric Littmann, Brooklyn, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 112 days.

(21) Appl. No.: 17/229,184

(22) Filed: Apr. 13, 2021

(65) Prior Publication Data

US 2021/0231657 A1    Jul. 29, 2021

Related U.S. Application Data

(63) Continuation of application No. PCT/US2019/056137, filed on Oct. 14, 2019.

(60) Provisional application No. 62/754,347, filed on Nov. 1, 2018, provisional application No. 62/745,343, filed on Oct. 13, 2018.

(51) Int. Cl.
*G01N 33/569* (2006.01)
*A61K 35/17* (2015.01)
*A61K 35/74* (2015.01)

(52) U.S. Cl.
CPC ........ *G01N 33/56911* (2013.01); *A61K 35/17* (2013.01); *A61K 35/74* (2013.01); *G01N 2496/00* (2013.01); *G01N 2800/52* (2013.01)

(58) Field of Classification Search
None
See application file for complete search history.

(56) References Cited

U.S. PATENT DOCUMENTS

| | | |
|---|---|---|
| 2017/0306416 A1 | 10/2017 | Bedoya et al. |
| 2018/0055892 A1 | 3/2018 | Mulder et al. |

FOREIGN PATENT DOCUMENTS

| | | |
|---|---|---|
| CN | 108130297 A | 6/2018 |
| WO | WO 2007/123488 A1 | 11/2007 |
| WO | WO 2016/057705 A1 | 4/2016 |
| WO | WO 2016/141454 A1 | 9/2016 |
| WO | WO 2016/160618 A2 | 10/2016 |
| WO | WO 2017/075537 A1 | 5/2017 |
| WO | WO 2017/091694 A1 | 6/2017 |
| WO | WO 2018/064165 A2 | 4/2018 |

OTHER PUBLICATIONS

Cong et al., "Roles of intestinal microbiota in response to cancer immunotherapy," European Journal of Clinical Microbiology & Infectious Diseases, 37(12):2235-2240 (2018).
Extended European Search Report dated Feb. 23, 2023 in Application No. EP 19871868.
Kuczma et al., "The impact of antibiotic usage on the efficacy of chemoimmunotherapy is contingent on the source of tumor-reactive T cells," Oncotarget, 8(67):111931-111942 (2017).
Grilli et al., "Isolation of Pseudobutyrivibrio ruminis and Pseudobutyrivibrio xylanivorans from Rumen of Creole Goats Fed Native Forage Diet," Folia Microbiol 58(5):1-10 (2012).
International Search Report dated Feb. 19, 2020 in International Application No. PCT/US19/56137.
Routy et al., "Gut Microbiome Influences Efficacy of PD-1-Based Immunotherapy Against Epithelial Tumors," Science 359:91-97 (2018).

*Primary Examiner* — Oluwatosin A Ogunbiyi
(74) *Attorney, Agent, or Firm* — Baker Botts L.L.P.

(57) ABSTRACT

The present invention relates to compositions, methods, and kits for predicting a subject's response to a CAR T cell therapy, by analyzing the intestinal microbiome of the subject. The present disclosure also provides a method of detecting patients at risk for a poor response to CAR T cell therapy by measuring the level of the presently disclosed bacteria or bacterial genes in the microflora or microbiome of a patient receiving or considered for CAR T cell therapy. The present disclosure further provides therapeutic compositions and methods for treating a subject having a cancer, by improving the subject's response to a CAR T cell therapy.

15 Claims, 18 Drawing Sheets

Figure 1:
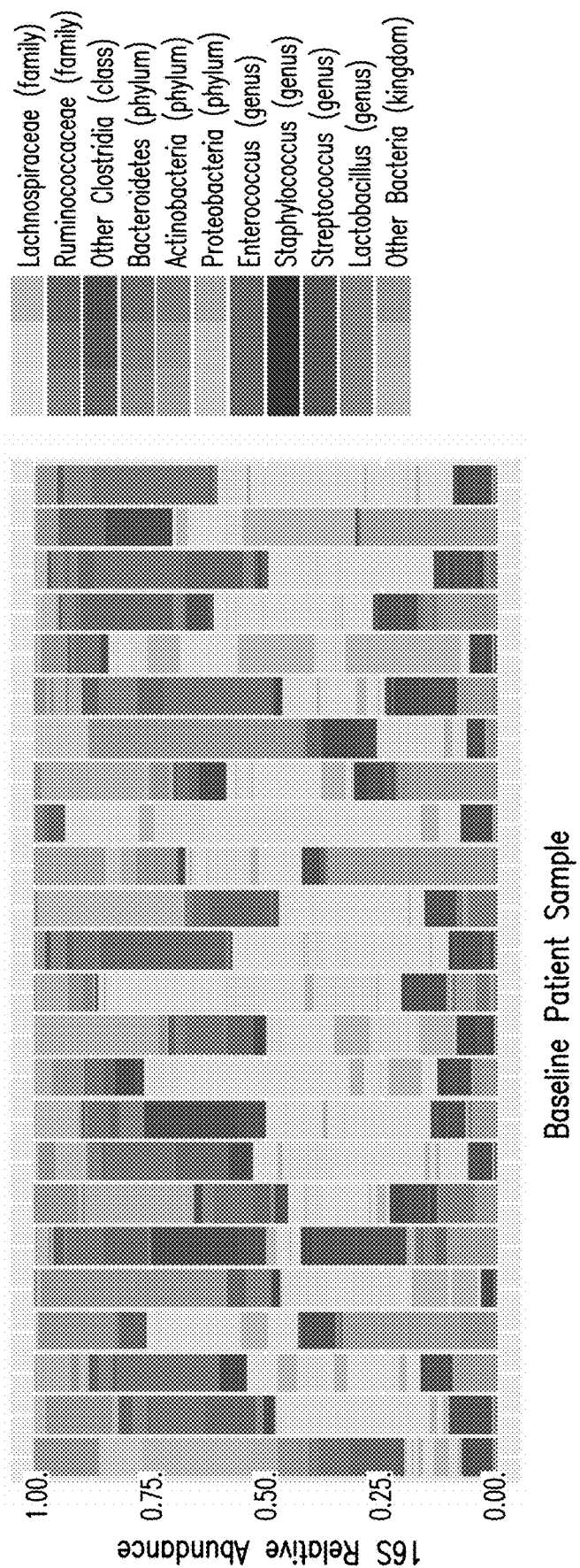

| Characteristic | N (%) |
|---|---|
| Age (median (range)) | 64.5 (38-79) |
| Gender = Male (%) | 27 (61.4) |
| *Disease (%)* | |
|   DLBCL | 24 (54.5) |
|   Multiple myeloma | 11 (25.0) |
|   CLL | 6 (13.6) |
|   ALL | 3 (6.0) |
| *CAR Construct* | |
|   Clinical Trial | 23 (52.3) |
|     BCMA | 11 (25.0) |
|     CD19 | 12 (27.3) |
|   Commercial | 21 (47.7) |
|     CD19 Axicabtagene Ciloleucel | 14 (31.8) |
|     CD19 Tisagenlecleucel | 7 (15.9) |
| *Prior Lines of Therapy (median (range))* | 5 (1-17) |

FIG. 11

| Outcome | N (%) |
|---|---|
| *Complete Response (%)* | |
| Yes | 20 (45.5) |
| No | 24 (54.5) |
| *Overall Response Rate (%)* | |
| Yes | 24 (54.5) |
| No | 18 (40.9) |
| Not Reached | 2 (4.5) |
| *Toxicity (%)* | |
| Yes | 32 (72.7) |
| No | 12 (28.3) |
| Cytokine Release Syndrome | 31 (70.5) |
| Grade 0 | 13 (29.5) |
| Grade 1 | 15 (34.1) |
| Grade 2 | 13 (29.5) |
| Grade 3 | 3 (6.8) |
| ICANS/Neurotoxicity | 10 (22.7) |
| Grade 0 | 34 (77.3) |
| Grade 1 | 5 (11.4) |
| Grade 2 | 3 (6.8) |
| Grade 3 | 2 (4.5) |

FIG. 12

METHODS AND COMPOSITIONS FOR IDENTIFYING AND TREATING SUBJECTS AT RISK FOR POOR CAR T CELL THERAPY RESPONSE

CROSS REFERENCE TO RELATED APPLICATIONS

This application is a continuation of International Application No. PCT/US2019/056137, filed Oct. 14, 2019, which claims priority to U.S. Provisional Application No. 62/745,343, filed on Oct. 13, 2018, and U.S. Provisional Application No. 62/754,347, filed on Nov. 1, 2018, the contents of each of which are incorporated by reference in their entireties, and to each of which priority is claimed.

STATEMENT OF GOVERNMENT INTEREST

This invention was made with government support under grant numbers AI124275, CA228308, and CA023766 awarded by the National Institutes of Health. The Government has certain rights in the invention.

1. TECHNICAL FIELD

The present invention relates to compositions, methods, and kits for predicting a subject's response to a CAR T cell therapy, by analyzing the intestinal microbiome of the subject. The present disclosure further provides therapeutic compositions and methods for treating a subject having a cancer, by improving the subject's response to a CAR T cell therapy.

2. BACKGROUND

The intestine of mammals is densely colonized by hundreds of microbial species that coexist symbiotically with their hosts. The microbes, collectively referred to as the intestinal microbiota, form the intestinal microbiome and contribute to numerous aspects of host health, including nutrient metabolism, homeostasis of intestinal tissues, development of innate and adaptive immune responses, and more generally, defense against intestinal infection. Healthy individuals harbor distinct microbial populations in their intestinal tract that vary markedly in composition.

3. SUMMARY

The present invention provides to compositions, methods, and kits for predicting a subject's response to a CAR T cell therapy. The present disclosure further provides therapeutic compositions and methods for treating a subject having a cancer, by improving the subject's response to a CAR T cell therapy.

In certain embodiments, the presently discloses provides a method for treating a subject having a cancer, comprising: (a) determining the level of a bacterium or spores thereof in a sample of the subject; (b) comparing the level of the bacterium or spores thereof to a reference bacterium or spores thereof level; (c) identifying the subject as likely to have a response to a CAR T cell therapy, or as likely to have no response or a poor response to the CAR T cell therapy, based on the comparison; and (d) administering the CAR T cell therapy to the subject identified as likely to have a response to the CAR T cell therapy, or administering a therapeutic bacterium or spores thereof or a pharmaceutical comprising thereof to the subject identified as likely to have no response or a poor response to the CAR T cell therapy, wherein the bacterium is selected from the group consisting of bacteria of the Peptostreptococcaceae family, bacteria of the Bacteroidaceae family, bacteria of the Clostridiaceae family, bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Peptococcaceae family and combinations thereof.

In certain embodiments, the subject is identified as likely to have a response to the CAR T cell therapy, if the level of the bacterium or spores thereof is lower than the reference bacterium or spores thereof level; or the subject is identified as likely to have no response or a poor response to the CAR T cell therapy, if the level of the bacterium or spores thereof is higher than the reference bacterium or spores thereof level; wherein the bacterium is selected from the group consisting of bacteria of the Peptostreptococcaceae family, bacteria of the Bacteroidaceae family, bacteria of the Clostridiaceae family, and any combinations thereof.

In certain embodiments, the presently discloses provides a method for treating a subject having a cancer comprising administering a CAR T cell therapy to the subject, wherein the subject is identified as likely to have a response to a CAR T cell therapy, and the level of a bacterium or spores thereof in a sample of the subject is lower than a reference bacterium or spores thereof level, wherein the bacterium is selected from the group consisting of bacteria of the Peptostreptococcaceae family, bacteria of the Bacteroidaceae family, bacteria of the Clostridiaceae family, and any combinations thereof.

In certain embodiments, the presently discloses provides a method for treating a subject having a cancer comprising administering a therapeutic bacterium or spores thereof or a pharmaceutical comprising thereof to the subject, wherein the subject is identified as likely to have no response or a poor response to a CAR T cell therapy, and the level of a bacterium or spores thereof in a sample of the subject is higher than a reference bacterium or spores thereof level, wherein the bacterium is selected from the group consisting of bacteria of the Peptostreptococcaceae family, bacteria of the Bacteroidaceae family, bacteria of the Clostridiaceae family, and any combinations thereof.

In certain embodiments, the bacteria of the Peptostreptococcaceae family comprise bacteria of the *Romboutsia* genus. In certain embodiments, the bacteria of the *Romboutsia* genus comprise *Romboutsia ileitis*. In certain embodiments, the bacteria of the Bacteroidaceae family comprise *Bacteroides uniformis*. In certain embodiments, the bacteria of the Clostridiaceae family comprise *Clostridium butyricum*.

In certain embodiments, the subject is identified as likely to have a response to the CAR T cell therapy, if the level of the bacterium or spores thereof is higher than the reference bacterium or spores thereof level; or the subject is identified as likely to have no response or a poor response to the CAR T cell therapy, if the level of the bacterium or spores thereof is lower than the reference bacterium or spores thereof level, wherein the bacterium is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof.

In certain embodiments, the presently discloses provides a method for treating a subject having a cancer comprising administering a CAR T cell therapy to the subject, wherein the subject is identified as likely to have a response to a CAR T cell therapy, and the level of a bacterium or spores thereof in a sample of the subject is higher than a reference bacterium or spores thereof level, wherein the bacterium is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof.

In certain embodiments, the presently discloses provides a method for treating a subject having a cancer comprising administering a therapeutic bacterium or spores thereof or a pharmaceutical comprising thereof to the subject, wherein the subject is identified as likely to have no response or a poor response to a CAR T cell therapy, and the level of a bacterium or spores thereof in a sample of the subject is lower than a reference bacterium or spores thereof level, wherein the bacterium is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof.

In certain embodiments, the bacteria of the Lachnospiraceae family comprise bacteria of the *Roseburia* genus, bacteria of the *Pseudobutyrivibrio* genus, bacteria of the *Lachnospira* genus, or a combination thereof. In certain embodiments, the bacteria of the *Pseudobutyrivibrio* genus comprise *Pseudobutyrivibrio ruminis*. In certain embodiments, the bacteria of the *Lachnospira* genus comprise *Lachnospira pectinoschiza, Coprococcus comes*, or a combination thereof. In certain embodiments, the bacteria of the Rikenellaceae family comprise *Alistipes indistinctus*. In certain embodiments, the bacteria of the Lactobacillaceae family comprise bacteria of the *Lactobacillus* genus. In certain embodiments, the bacteria of the *Lactobacillus* genus comprise *Lactobacillus fermentum, Lactobacillus rogosae*, or a combination thereof. In certain embodiments, the bacteria of the Oscillospiraceae family comprise *Oscillibacter valericigenes*. In certain embodiments, the bacteria of the Ruminococcaceae family comprise bacteria of the *Anaerotruncus* genus, bacteria of the Ruminococcaceae UCG-004 genus, or a combination thereof. In certain embodiments, the bacteria of the *Anaerotruncus* genus comprise *Anaerotruncus colihominis, Clostridium methylpentosum*, or a combination thereof. In certain embodiments, the bacteria of the Acidaminococcaceae family comprise bacteria of the *Phascolarctobacterium* genus. In certain embodiments, the bacteria of the *Phascolarctobacterium* genus comprise *Phascolarctobacterium faecium*. In certain embodiments, the bacteria of the Clostridiaceae family comprise *Clostridium amygdalinum, Clostridium saccharolyticum*, or a combination thereof.

In certain embodiments, the level of the bacterium or spores thereof is the relative abundance of the bacterium or spores thereof as compared to other bacteria in the sample In certain embodiments, the presently discloses provides a method for treating a subject having a cancer, comprising: (a) determining the level of a bacterial gene in a sample of the subject; (b) comparing the level of the bacterial gene to a reference bacterial gene level; (c) identifying the subject as likely to have a response to a CAR T cell therapy, or as likely to have no response or a poor response to the CAR T cell therapy, based on the comparison; and (d) administering the CAR T cell therapy to the subject identified as likely to have a response to the CAR T cell therapy, or administering a therapeutic bacterium or spores thereof or a pharmaceutical comprising thereof to the subject identified as likely to have no response or a poor response to the CAR T cell therapy, wherein the bacterial gene is selected from the group consisting of genes involved in vitamin B biosynthesis or secondary bile acid biosynthesis or degradation.

In certain embodiments, the subject is identified as likely to have a response to the CAR T cell therapy, if the level of the bacterial gene is lower than the reference bacterial gene level; or the subject is identified as likely to have no response or a poor response to the CAR T cell therapy, if the level of the bacterial gene is higher than the reference bacterial gene level.

In certain embodiments, the presently discloses provides a method for treating a subject having a cancer comprising administering a CAR T cell therapy to the subject, wherein the subject is identified as likely to have a response to a CAR T cell therapy, and the level of a bacterial gene in a sample of the subject is lower than a reference bacterial gene level, wherein the bacterial gene is selected from the group consisting of genes involved in vitamin B biosynthesis or secondary bile acid biosynthesis or degradation.

In certain embodiments, the presently discloses provides a method for treating a subject having a cancer comprising administering a therapeutic bacterium or spores thereof or a pharmaceutical comprising thereof to the subject, wherein the subject is identified as likely to have no response or a poor response to a CAR T cell therapy, and the level of a bacterial gene in a sample of the subject is higher than a reference bacterial gene level, wherein the bacterial gene is selected from the group consisting of genes involved in vitamin B biosynthesis or secondary bile acid biosynthesis or degradation.

In certain embodiments, the genes involved in B vitamin biosynthesis include thiH, panC, pdxJ, gapA, dxs, or a combination thereof. In certain embodiments, the genes involved in secondary bile acid biosynthesis and degradation include baiA1, baiF, baiE, baiCD, or a combination thereof.

In certain embodiments, the level of the bacterial gene is the relative abundance of the bacterial gene as compared to other bacterial genes in the sample.

In certain embodiments, the sample is a fecal sample or an intestinal content sample of the subject.

In certain embodiments, the cancer is an ovarian cancer, a multiple myeloma, a B-cell malignancy, or a combination thereof.

In certain embodiments, the CAR T cell therapy comprises a CAR T cell comprising an extracellular binding domain that binds to mucin 16 (MUC16), B-cell maturation antigen (BCMA), CD19, or a combination thereof.

In certain embodiments, the therapeutic bacterium or spores thereof is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof.

In certain embodiments, the subject is receiving, will receive, or have received the CAR T cell therapy.

In certain embodiments, the response to the CAR T cell therapy is a partial response or a complete response.

In certain embodiments, the presently discloses provides a pharmaceutical composition comprising a therapeutic bacterium or spores thereof, and a biocompatible pharmaceutical carrier, wherein the therapeutic bacterium or spores thereof is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof.

In certain embodiments, the bacteria of the Lachnospiraceae family comprise bacteria of the *Roseburia* genus, bacteria of the *Pseudobutyrivibrio* genus, bacteria of the *Lachnospira* genus, or a combination thereof. In certain embodiments, the bacteria of the *Pseudobutyrivibrio* genus comprise *Pseudobutyrivibrio ruminis*. In certain embodiments, the bacteria of the *Lachnospira* genus comprise *Lachnospira pectinoschiza, Coprococcus comes*, or a combination thereof. In certain embodiments, the bacteria of the Rikenellaceae family comprise *Alistipes indistinctus*. In certain embodiments, the bacteria of the Lactobacillaceae family comprise bacteria of the *Lactobacillus* genus. In certain embodiments, the bacteria of the *Lactobacillus* genus comprise *Lactobacillus fermentum, Lactobacillus rogosae*, or a combination thereof. In certain embodiments, the bacteria of the Oscillospiraceae family comprise *Oscillibacter valericigenes*. In certain embodiments, the bacteria of the Ruminococcaceae family comprise bacteria of the *Anaerotruncus* genus, bacteria of the Ruminococcaceae UCG-004 genus, or a combination thereof. In certain embodiments, the bacteria of the *Anaerotruncus* genus comprise *Anaerotruncus colihominis, Clostridium methylpentosum*, or a combination thereof. In certain embodiments, the bacteria of the Acidaminococcaceae family comprise bacteria of the *Phascolarctobacterium* genus. In certain embodiments, the bacteria of the *Phascolarctobacterium* genus comprise *Phascolarctobacterium faecium*. In certain embodiments, the bacteria of the Clostridiaceae family comprise *Clostridium amygdalinum, Clostridium saccharolyticum*, or a combination thereof.

In certain embodiments, the presently discloses provides a method for identifying a subject having a cancer as likely to have a response to a CAR T cell therapy, or as likely to have no response or a poor response to the CAR T cell therapy: (a) determining the level of a bacterium or spores thereof in a sample of the subject; (b) comparing the level of the bacterium or spores thereof to a reference bacterium or spores thereof level; (c) identifying the subject as likely to have a response to the CAR T cell therapy, or as likely to have no response or a poor response to the CAR T cell therapy, based on the comparison, wherein the bacterium is selected from the group consisting of bacteria of the Peptostreptococcaceae family, bacteria of the Bacteroidaceae family, bacteria of the Clostridiaceae family, bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Peptococcaceae family and combinations thereof.

In certain embodiments, the subject is identified as likely to have a response to the CAR T cell therapy, if the level of the bacterium or spores thereof is lower than the reference bacterium or spores thereof level; or the subject is identified as likely to have no response or a poor response to the CAR T cell therapy, if the level of the bacterium or spores thereof is higher than the reference bacterium or spores thereof level; wherein the bacterium is selected from the group consisting of bacteria of the Peptostreptococcaceae family, bacteria of the Bacteroidaceae family, bacteria of the Clostridiaceae family, and any combinations thereof.

In certain embodiments, the bacteria of the Peptostreptococcaceae family comprise bacteria of the *Romboutsia* genus. In certain embodiments, the bacteria of the *Romboutsia* genus comprise *Romboutsia ileitis*. In certain embodiments, the bacteria of the Bacteroidaceae family comprise *Bacteroides uniformis*. In certain embodiments, the bacteria of the Clostridiaceae family comprise *Clostridium butyricum*.

In certain embodiments, the subject is identified as likely to have a response to the CAR T cell therapy, if the level of the bacterium or spores thereof is higher than the reference bacterium or spores thereof level; or the subject is identified as likely to have no response or a poor response to the CAR T cell therapy, if the level of the bacterium or spores thereof is lower than the reference bacterium or spores thereof level, wherein the bacterium is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof.

In certain embodiments, the bacteria of the Lachnospiraceae family comprise bacteria of the *Roseburia* genus, bacteria of the *Pseudobutyrivibrio* genus, bacteria of the *Lachnospira* genus, or a combination thereof. In certain embodiments, the bacteria of the *Pseudobutyrivibrio* genus comprise *Pseudobutyrivibrio ruminis*. In certain embodiments, the bacteria of the *Lachnospira* genus comprise *Lachnospira pectinoschiza, Coprococcus comes*, or a combination thereof. In certain embodiments, the bacteria of the Rikenellaceae family comprise *Alistipes indistinctus*. In certain embodiments, the bacteria of the Lactobacillaceae family comprise bacteria of the *Lactobacillus* genus. In certain embodiments, the bacteria of the *Lactobacillus* genus comprise *Lactobacillus fermentum, Lactobacillus rogosae*, or a combination thereof. In certain embodiments, the bacteria of the Oscillospiraceae family comprise *Oscillibacter valericigenes*. In certain embodiments, the bacteria of the Ruminococcaceae family comprise bacteria of the *Anaerotruncus* genus, bacteria of the Ruminococcaceae UCG-004 genus, or a combination thereof. In certain embodiments, the bacteria of the *Anaerotruncus* genus comprise *Anaerotruncus colihominis, Clostridium methylpentosum*, or a combination thereof. In certain embodiments, the bacteria of the Acidaminococcaceae family comprise bacteria of the *Phascolarctobacterium* genus. In certain embodiments, the bacteria of the *Phascolarctobacterium* genus comprise *Phascolarctobacterium faecium*. In certain embodiments, the bacteria of the Clostridiaceae family comprise *Clostridium amygdalinum, Clostridium saccharolyticum*, or a combination thereof.

In certain embodiments, the level of the bacterium or spores thereof is the relative abundance of the bacterium or spores thereof as compared to other bacteria in the sample In certain embodiments, the presently discloses provides a method for identifying the subject having a cancer as likely to have a response to a CAR T cell therapy, or as likely to have no response or a poor response to the CAR T cell therapy, comprising: (a) determining the level of a bacterial gene in a sample of the subject; (b) comparing the level of the bacterial gene to a reference bacterial gene level; and (c) identifying the subject as likely to have a response to the CAR T cell therapy, or as likely to have no response or a poor response to the CAR T cell therapy, based on the comparison; wherein the bacterial gene is selected from the group consisting of genes involved in vitamin B biosynthesis or secondary bile acid biosynthesis or degradation.

In certain embodiments, the subject is identified as likely to have a response to the CAR T cell therapy, if the level of the bacterial gene is lower than the reference bacterial gene level; or the subject is identified as likely to have no response or a poor response to the CAR T cell therapy, if the level of the bacterial gene is higher than the reference bacterial gene level.

In certain embodiments, the genes involved in B vitamin biosynthesis include thiH, panC, pdxJ, gapA, dxs, or a combination thereof. In certain embodiments, the genes involved in secondary bile acid biosynthesis and degradation include baiA1, baiF, baiE, baiCD, or a combination thereof.

In certain embodiments, the level of the bacterial gene is the relative abundance of the bacterial gene as compared to other bacterial genes in the sample.

In certain embodiments, the sample is a fecal sample or an intestinal content sample of the subject.

In certain embodiments, the cancer is an ovarian cancer, a multiple myeloma, a B-cell malignancy, or a combination thereof.

In certain embodiments, the CAR T cell therapy comprises a CAR T cell comprising an extracellular binding domain that binds to mucin 16 (MUC16), B-cell maturation antigen (BCMA), CD19, or a combination thereof.

In certain embodiments, the subject is receiving, will receive, or have received the CAR T cell therapy.

In certain embodiments, the response to the CAR T cell therapy is a partial response or a complete response.

In certain embodiments, the presently discloses provides a kit for of identifying a subject as likely to have a response to a CAR T cell therapy, or as likely to have no response or a poor response to the CAR T cell therapy, wherein the kit comprising means for detecting the level of a bacterium or spores thereof, wherein the bacterium is selected from the group consisting of bacteria of the Peptostreptococcaceae family, bacteria of the Bacteroidaceae family, bacteria of the Clostridiaceae family, bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Peptococcaceae family and combinations thereof.

In certain embodiments, the presently disclosed kits further comprise instructions for identifying the subjects as likely to have a response to the CAR T cell therapy, or as likely to have no response or a poor response to the CAR T cell therapy, wherein the instructions comprise: (a) determining the level of the bacterium or spores thereof in a sample of the subject; (b) comparing the level of the bacterium or spores thereof to a reference bacterium or spores thereof level; and (c) identifying the subject as likely to have a response to the CAR T cell therapy, or as likely to have no response or a poor response to the CAR T cell therapy, based on the comparison.

In certain embodiments, the presently discloses provides a kit for of identifying a subject as likely to have a response to a CAR T cell therapy, or as likely to have no response or a poor response to the CAR T cell therapy, wherein the kit comprising means for detecting the level of a bacterial gene, wherein the bacterial gene is selected from the group consisting of genes involved in vitamin B biosynthesis or secondary bile acid biosynthesis or degradation.

In certain embodiments, the presently disclosed kits further comprise instructions for identifying the subjects as likely to have a response to the CAR T cell therapy, or as likely to have no response or a poor response to the CAR T cell therapy, wherein the instructions comprise: (a) determining the level of the bacterial gene in a sample of the subject; (b) comparing the level of the bacterial gene to a reference bacterium or spores thereof level; and (c) identifying the subject as likely to have a response to the CAR T cell therapy, or as likely to have no response or a poor response to the CAR T cell therapy, based on the comparison.

The present disclosure provides a pharmaceutical composition including one or more isolated bacteria or spores thereof, wherein the isolated bacteria or spores thereof are a member of the Lachnospiraceae family, the Rikenellaceae family, the Lactobacillaceae family, the Oscillospiraceae family, the Ruminococcaceae family, or the Acidaminococcaceae family and a biocompatible pharmaceutical carrier.

The pharmaceutical composition can have the following additional features, which can be combined with one another and with other aspects of the specification unless clearly mutually exclusive:

i) the isolated bacteria or spores thereof can be a member of the Lachnospiraceae family;
ii) the isolated bacteria or spores thereof can be a member of the *Pseudobutyrivibrio* genus;
iii) the isolated bacteria or spores thereof can be *Pseudobutyrivibrio ruminis*;
iv) the isolated bacteria or spores thereof can be a member of the *Lachnospira* genus;
v) the isolated bacteria or spores thereof can be *Lachnospira pectinoschiza*;
vi) the isolated bacteria or spores thereof can be *Clostridium amygdalinum, Clostridium saccharolyticum*, or *Coprococcus comes*;
vii) the isolated bacteria or spores thereof can be a member of the Lachnospiraceae family;
viii) the isolated bacteria or spores thereof can be a member of the Rikenellaceae family;
ix) the isolated bacteria or spores thereof can be *Alistipes indistinctus*;
x) the isolated bacteria or spores thereof can be a member of the Lactobacillaceae family;
xi) the isolated bacteria or spores thereof can be a member of the *Lactobacillus* genus;
xii) the isolated bacteria or spores thereof can be *Lactobacillus fermentum* or *Lactobacillus rogosae*;
xiii) the isolated bacteria or spores thereof can be a member of the Oscillospiraceae family;
xiv) the isolated bacteria or spores thereof can be *Oscillibacter valericigenes*;
xv) the isolated bacteria or spores thereof can be a member of the Ruminococcaceae family;
xvi) the isolated bacteria or spores thereof can be a member of the *Anaerotruncus* genus;
xvii) the isolated bacteria or spores thereof can be *Anaerotruncus colihominis*;
xviii) the isolated bacteria or spores thereof can be a member of the Acidaminococcaceae family;
xix) the isolated bacteria or spores thereof can be a member of the *Phascolarctobacterium* genus;
xx) the isolated bacteria or spores thereof can be *Phascolarctobacterium faecium*;

The present disclosure also provides a method of identifying patients at higher risk of a poor response to a CAR T cell therapy by determining the level of one or more bacteria or spores thereof of the Peptostreptococcaceae family, the Bacteroidaceae family, the Clostridiaceae family, the Lachnospiraceae family, the Rikenellaceae family, the Lactobacillaceae family, the Oscillospiraceae family, the Ruminococcaceae family, or the Acidaminococcaceae family, or the level of a bacterial vitamin B biosynthesis or secondary bile acid biosynthesis or degradation gene in an intestinal microbiome in a fecal sample of a patient, comparing the level of the one or more bacteria or spores or bacterial genes therein with at least one reference bacteria level or reference bacterial gene level, and identifying the patient as at higher risk of a poor response to the CAR T cell therapy if the level of bacteria or spores thereof of the Peptostreptococcaceae family, the Bacteroidaceae family, the Clostridiaceae family, bacterial vitamin B biosynthesis gene, secondary bile acid biosynthesis gene, or secondary bile acid degradation gene is greater than the reference level, or if the level of bacteria or spores of the Lachnospiraceae family, the Rikenellaceae family, the Lactobacillaceae family, the Oscillospiraceae family, the Ruminococcaceae family, or the Acidaminococcaceae family is lower than the reference level.

The method can have the following additional features, which can be combined with one another and with other aspects of the specification unless clearly mutually exclusive:

i) the reference bacteria level can be based on relative abundance of the bacteria or spores thereof as compared to other bacteria in the intestinal microbiome;

ii) the reference bacterial gene level can be based on relative abundance of the bacterial gene as compared to other bacterial genes in the intestinal microbiome;

iii) the method can include determining the level of two or more bacteria or spores thereof or bacterial genes;

iv) the method can include determining the level of a bacterial vitamin B biosynthesis gene by determining the level of one or more of a thiamine (thiH), pantothenic acid (panC), or pyroxidine (pdxJ, gapA, dxs) gene.

The present disclosure also includes a method of treating a patient with at risk of exhibiting a poor response to a CAR T cell therapy by diagnosing the subject as having a higher risk of exhibiting a poor response to the CAR T cell therapy using the of the methods described above or otherwise in the present specification and administering to the subject any pharmaceutical composition described above or otherwise in the present specification. The patient can suffer from a CD19 malignancy, myeloma, or ovarian cancer.

The present disclosure also provides a kit for identifying subjects at risk of exhibiting a poor response to a CAR T cell therapy, the kit comprising means for detecting the level of one or more bacterial or spores or bacterial genes identified in the methods described above or otherwise in the present specification according to such methods. The kit may also include any pharmaceutical composition as described above or otherwise in the present specification. The means for detecting can include at least one nucleic acid primer, at least one nucleic acid probe, at least one antibody, or any combinations thereof. The kit can include any composition described above, which can be administered in any administering step described above.

4. BRIEF DESCRIPTION OF THE FIGURES

For a more complete understanding of the present disclosure and its features and advantages, reference is now made to the following description, taken in conjunction with the accompanying drawings. The patent or application file contains at least one drawing executed in color. Copies of this patent or patent application publication with color drawing(s) will be provided by the Office upon request and payment of the necessary fee.

FIG. 1 provides a graph showing relative 16S RNA abundance for various bacterial families in a representative CAR T cell therapy patient prior to administration of genetically modified T cells.

Figure 2:
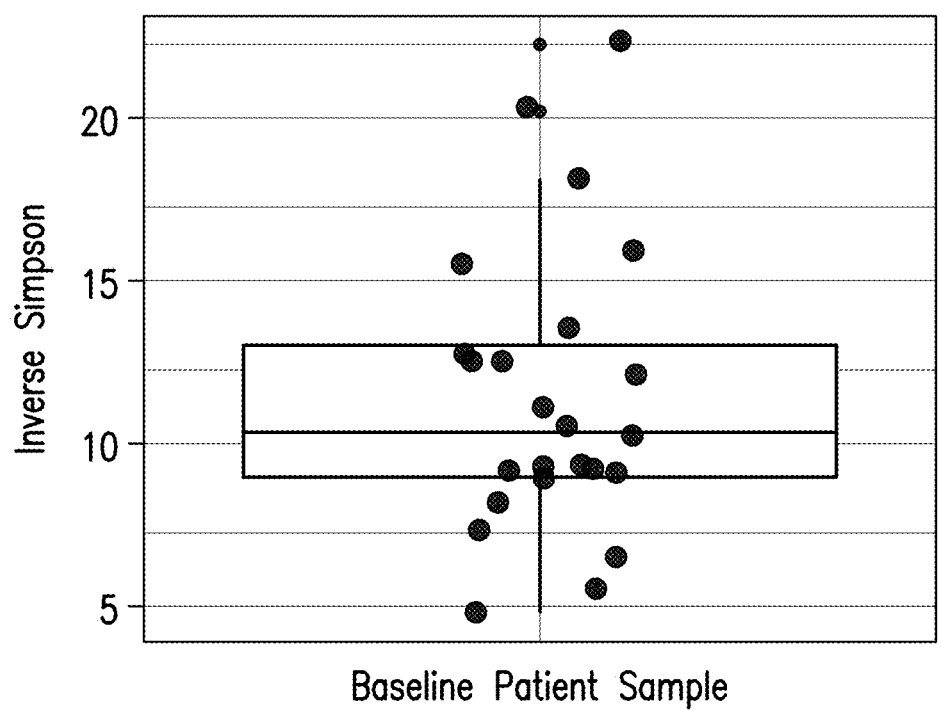

FIG. 2 provides a graph showing the inverse Simpson diversity index for each of twenty-four patients prior to administration of genetically modified T cells in CAR T cell therapy.

Figure 3:
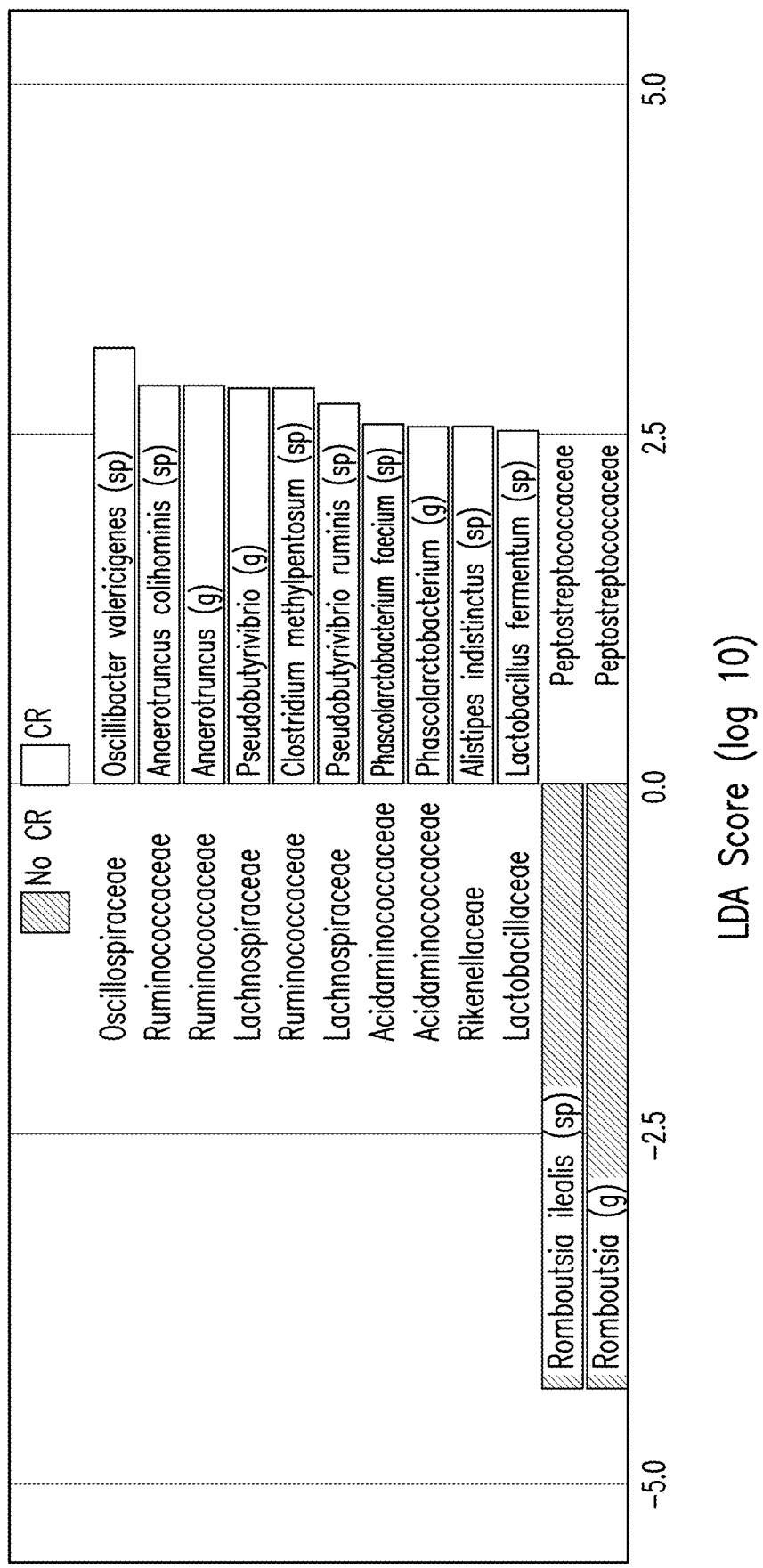

FIG. 3 provides a graph showing linear discriminant analysis effect size (LEfSe) results with respect to various microbiota in patients who achieved a complete response (CR) to CAR T cell therapy and those who did not achieve a complete response (no CR) to CAR T cell therapy.

Figure 4:
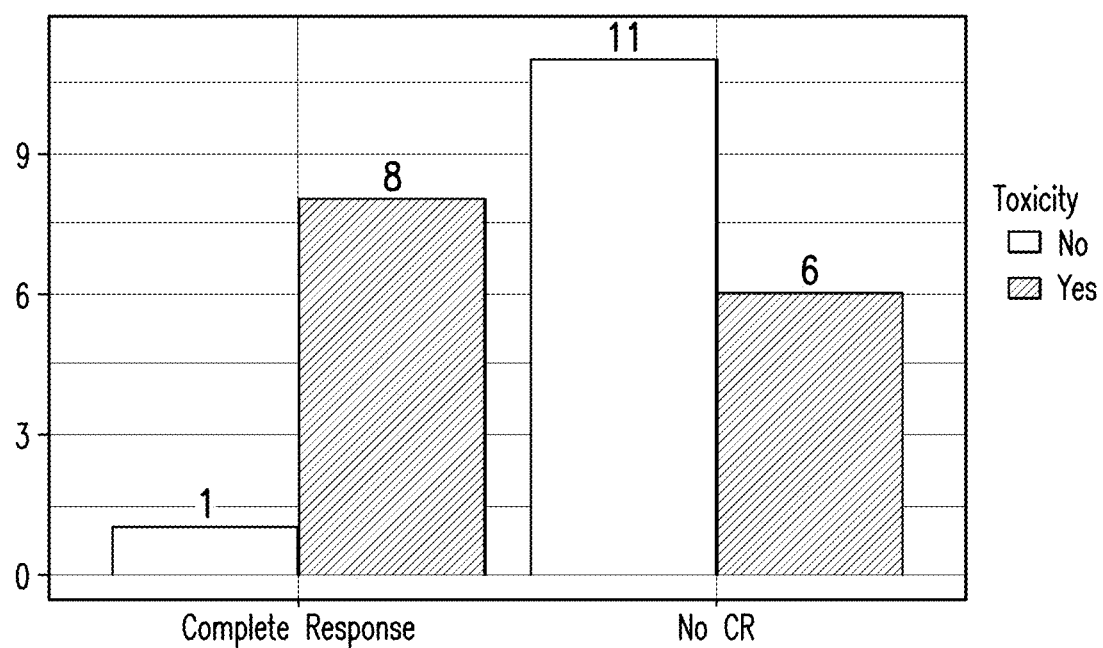

FIG. 4 provides a graph showing the number of patients who exhibited a complete response to CAR T cell therapy who also exhibited toxicity and the number of patients who exhibited no complete response to CAR T cell therapy (no CR) and who also exhibited toxicity.

Figure 5:
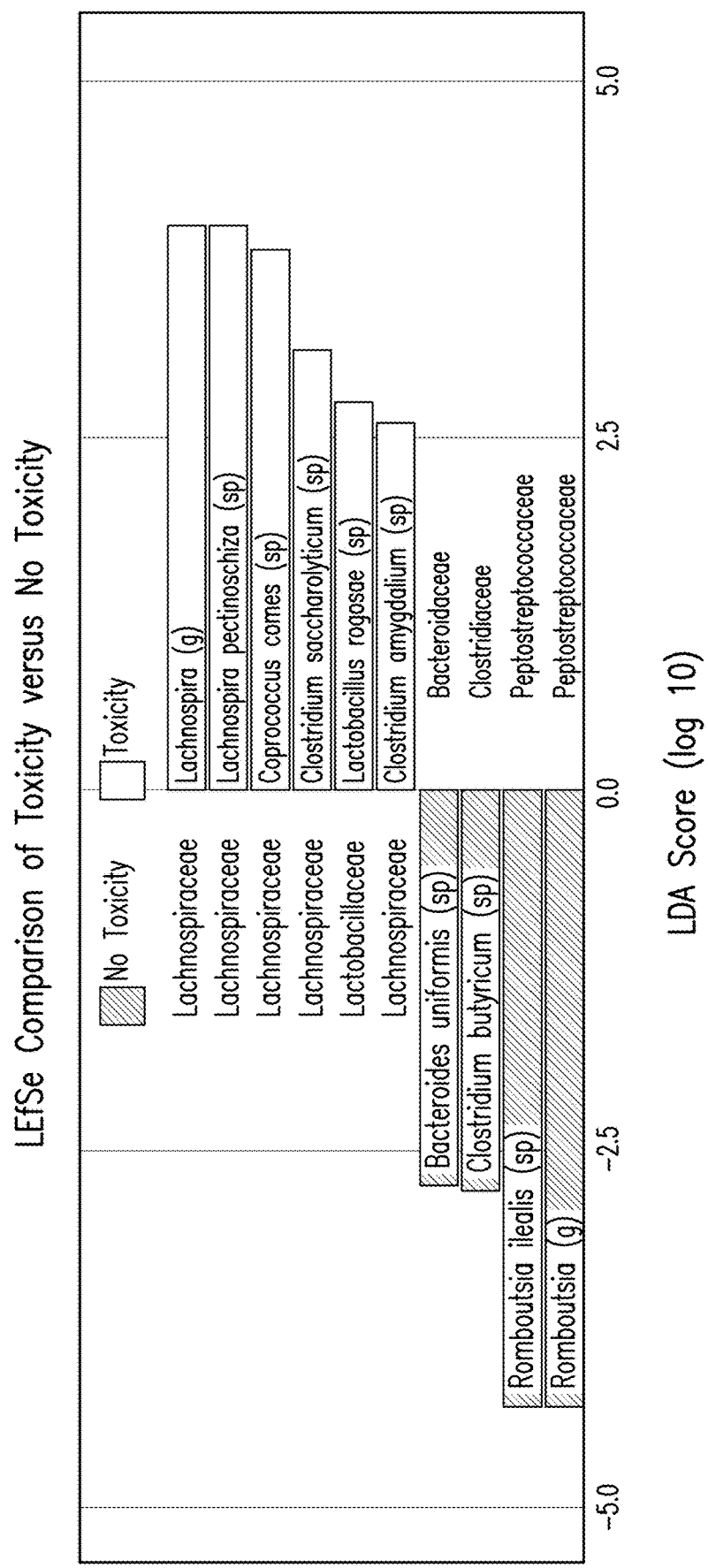

FIG. 5 provides a graph showing LEfSe results with respect to various microbiota in patients who exhibited toxicity or did not exhibit toxicity after being administered genetically modified T cells in CAR T cell therapy.

Figure 6:
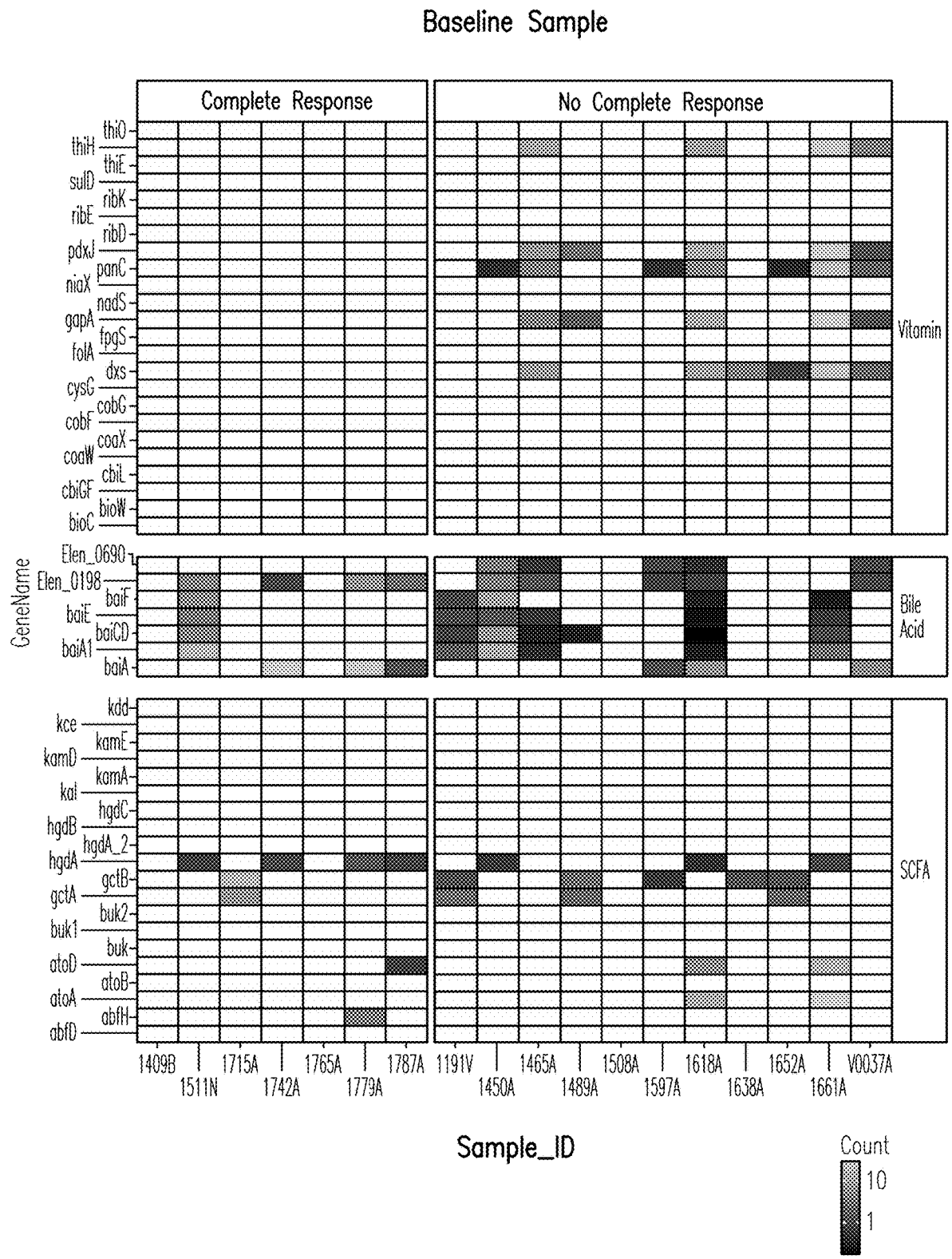

FIG. 6 provides a heatmap showing, by patient sample in patients exhibiting a complete response (CR) or no complete response (noCR), relative prevalence of bacterial genes associated with B vitamin synthesis, secondary bile acid biosynthesis and degradation, and short chain fatty acid (SCFA) biosynthesis.

Figure 7:
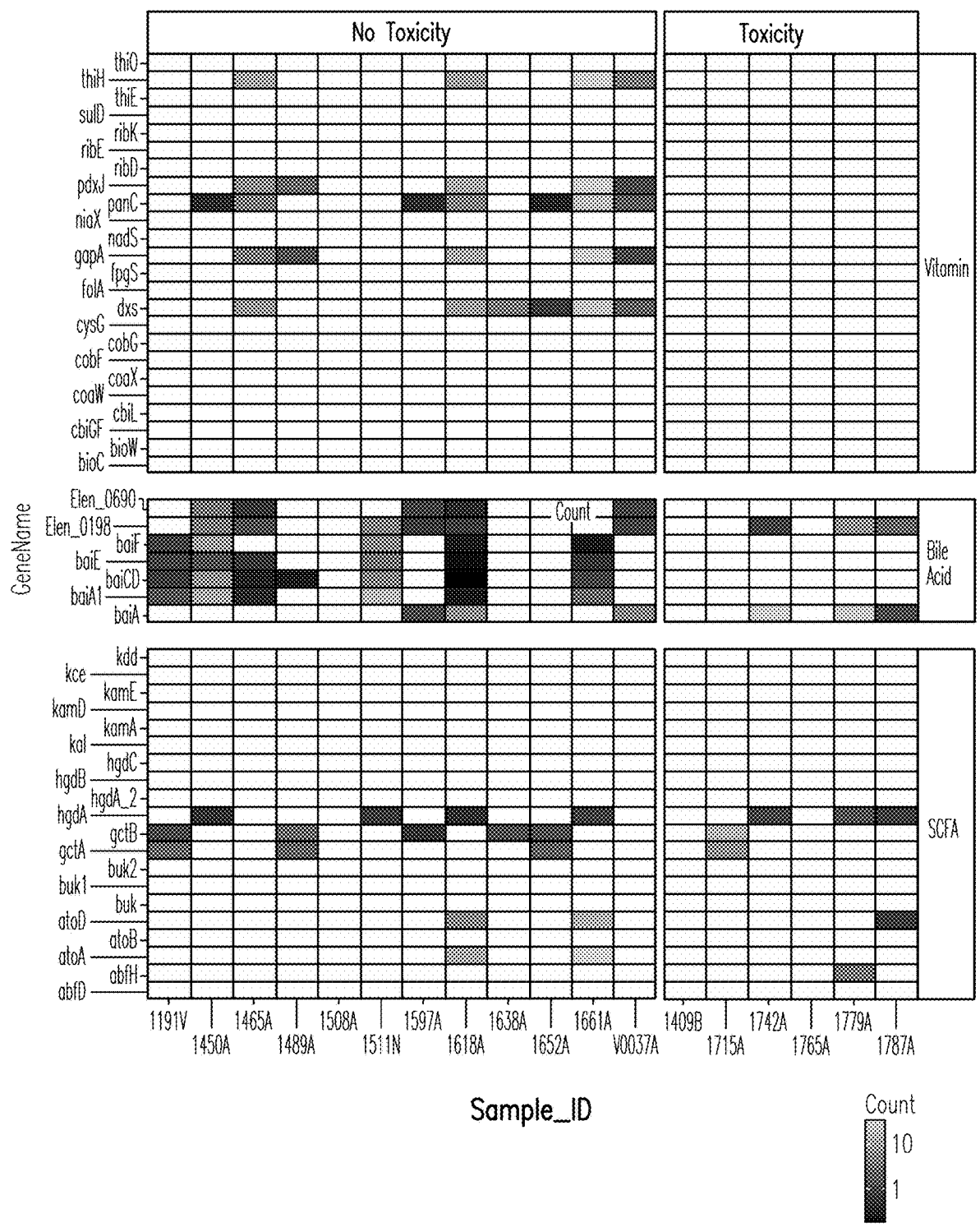

FIG. 7 provides a heatmap showing, by patient sample in patients exhibiting toxicity or no toxicity, relative prevalence of bacterial genes associated with B vitamin synthesis, secondary bile acid biosynthesis and degradation, and short chain fatty acid (SCFA) biosynthesis.

Figure 8:
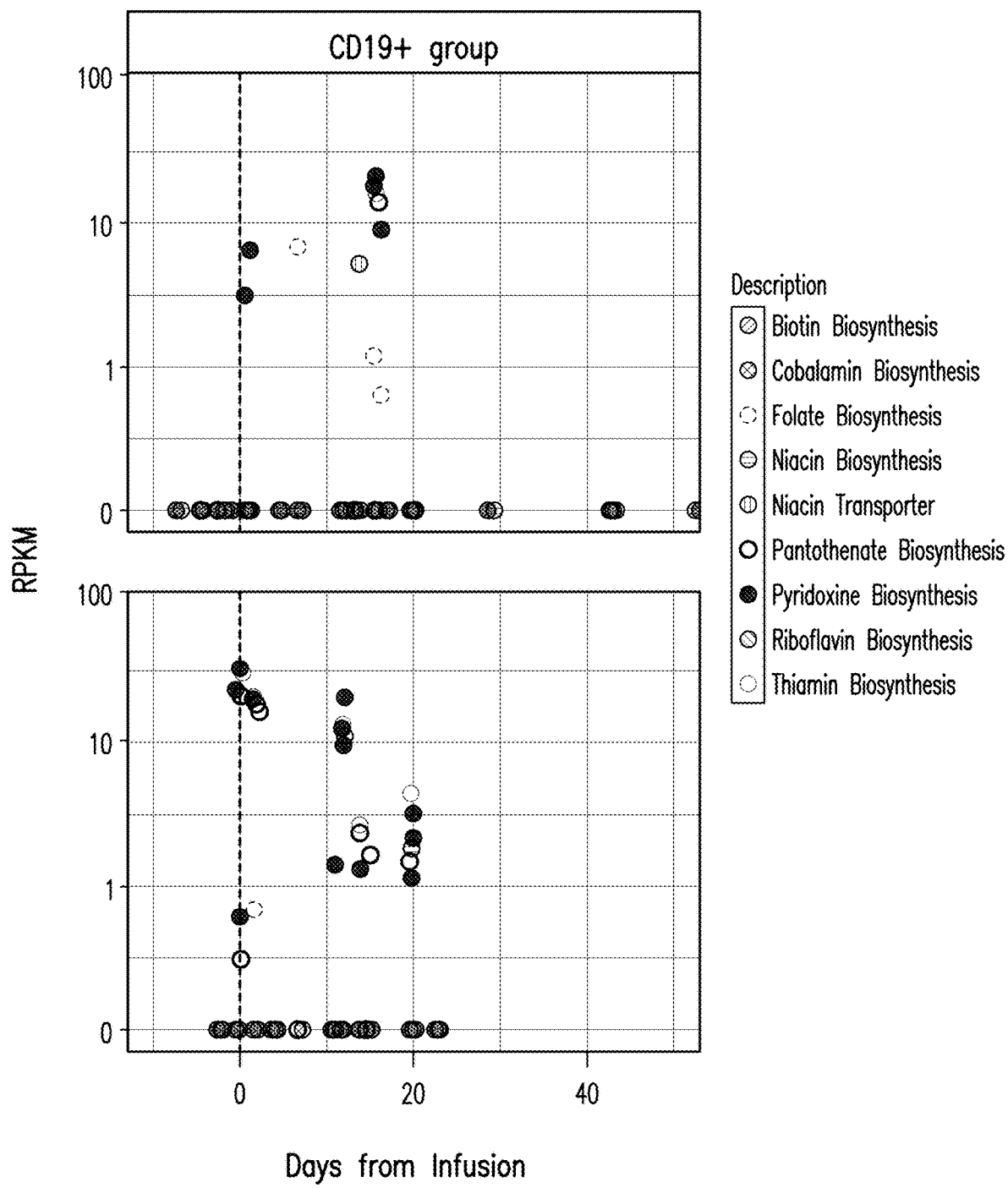
Figure 8:
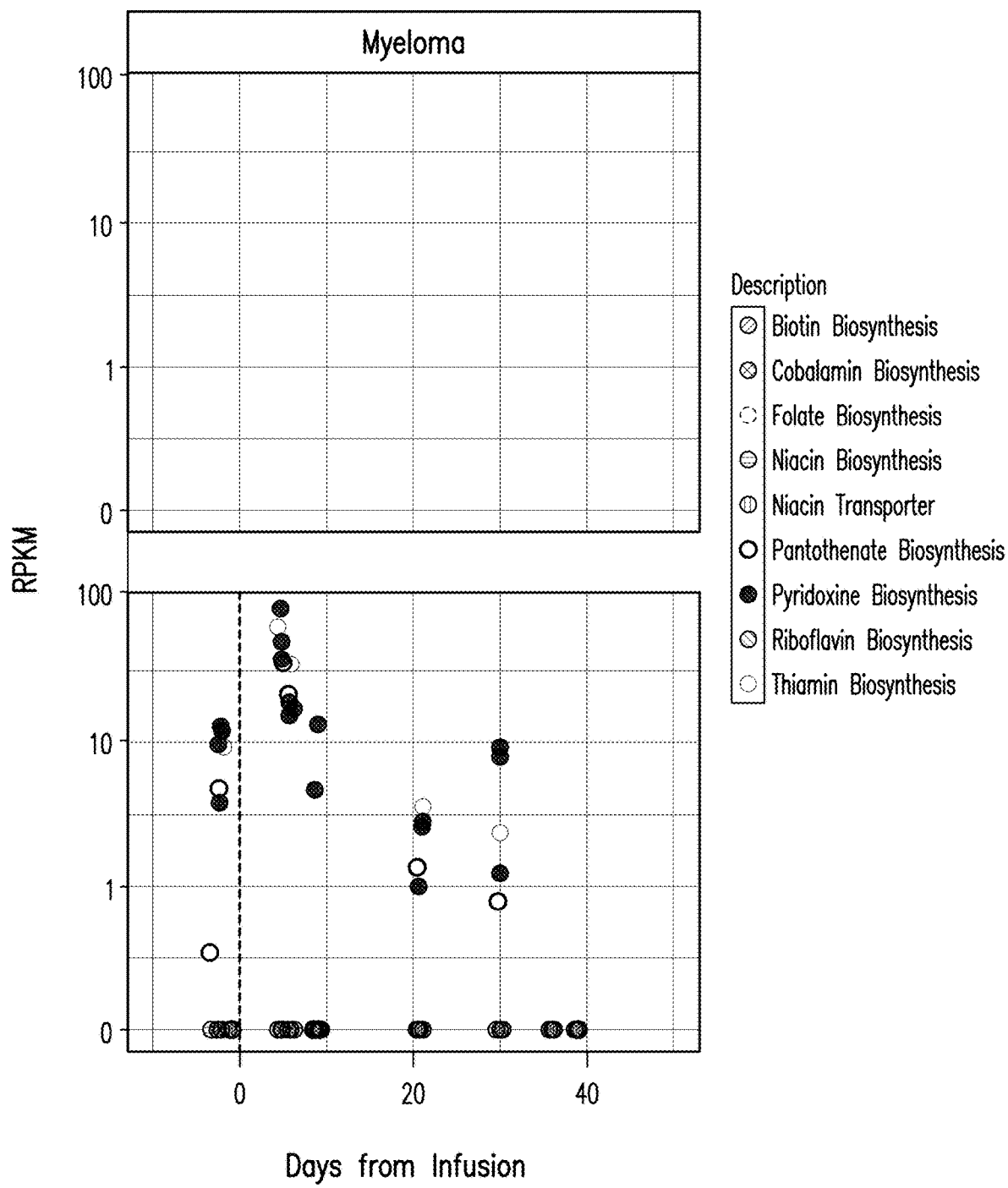
Figure 8:
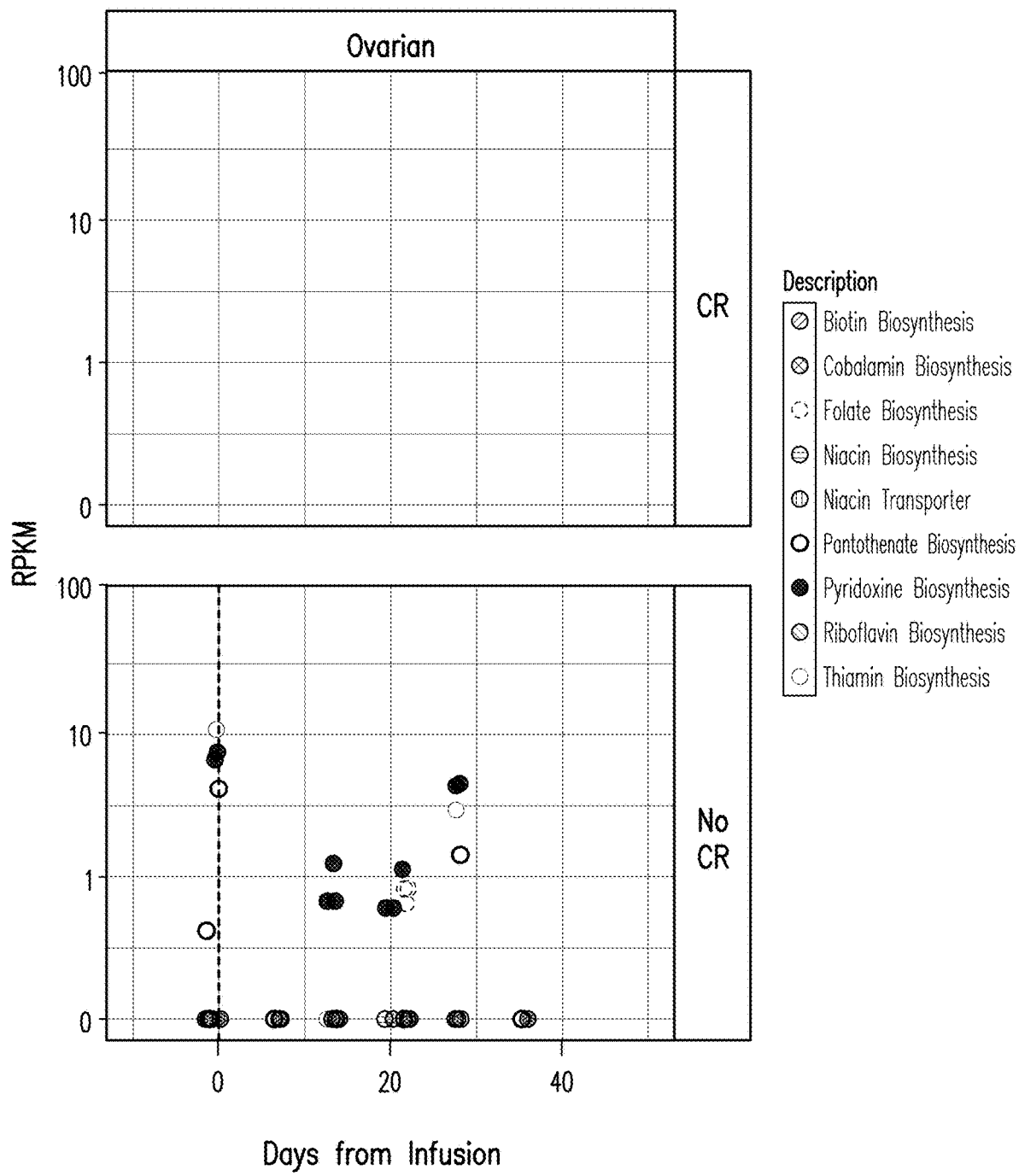

FIG. 8 provides a graph showing relative abundance of bacterial genes associated with biosynthesis of various B vitamins in patients with different types of cancer who exhibited a complete response (CR) or did not exhibit a complete response (no CR) to CAR T cell therapy.

Figure 9:
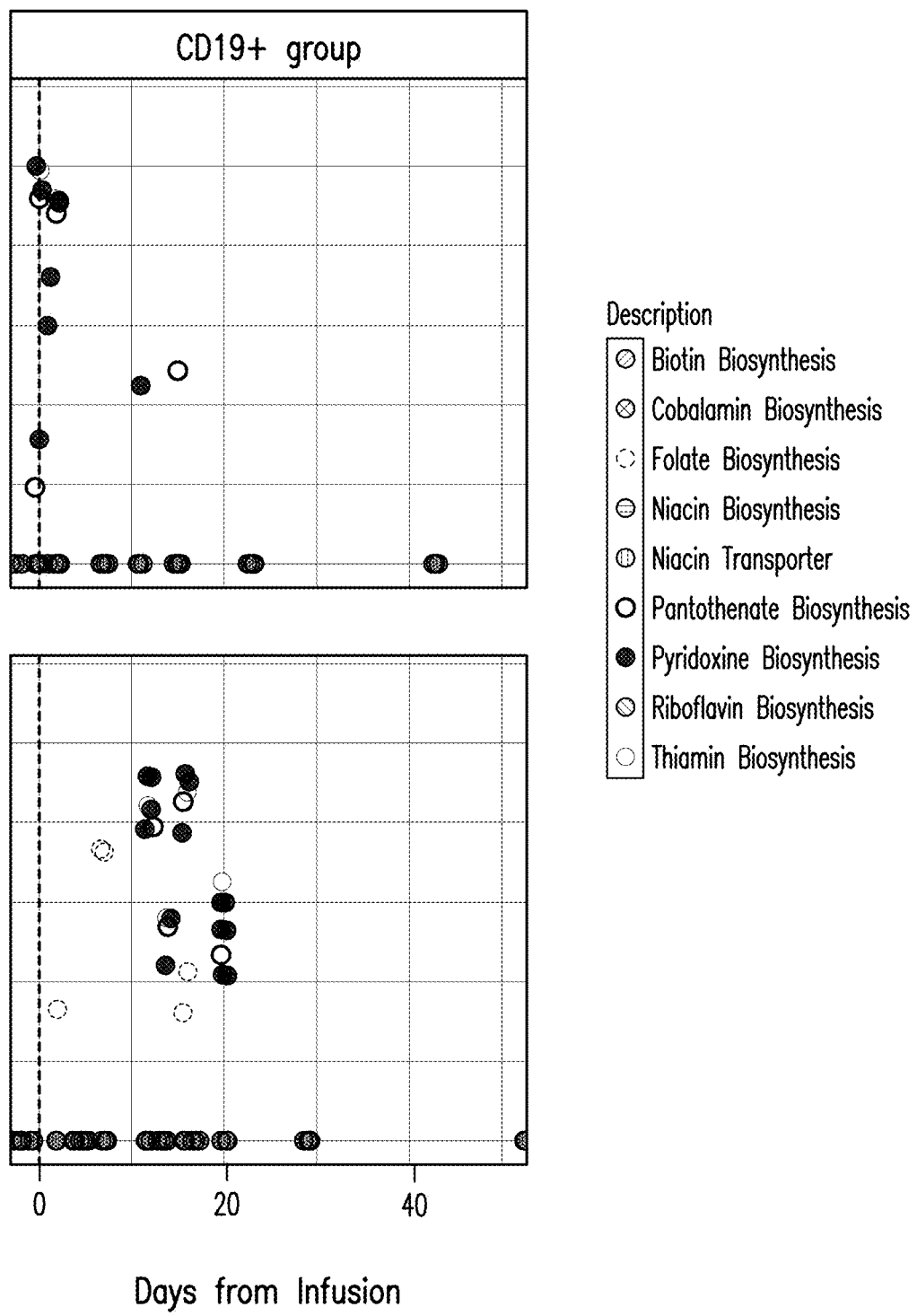
Figure 9:
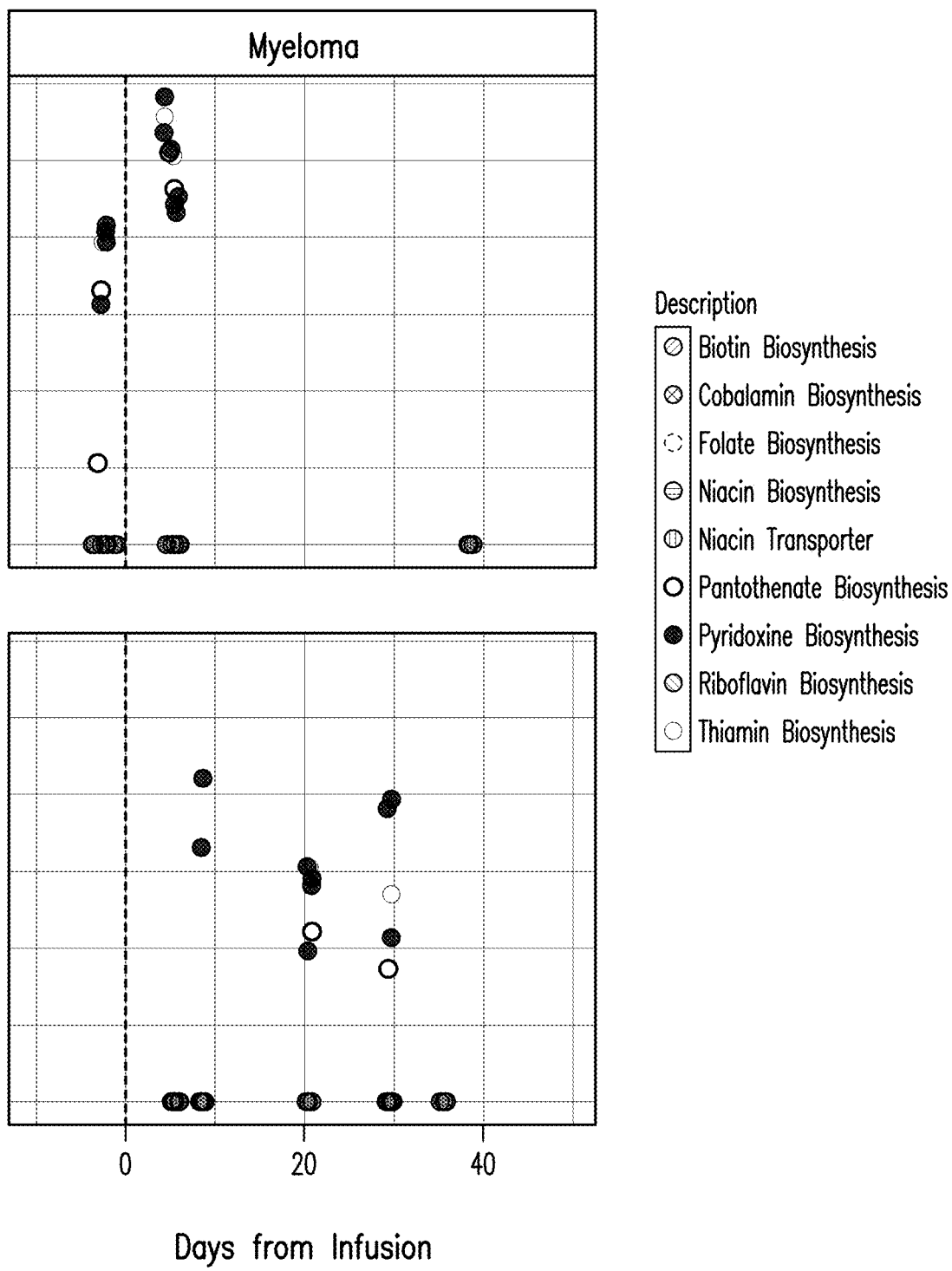
Figure 9:
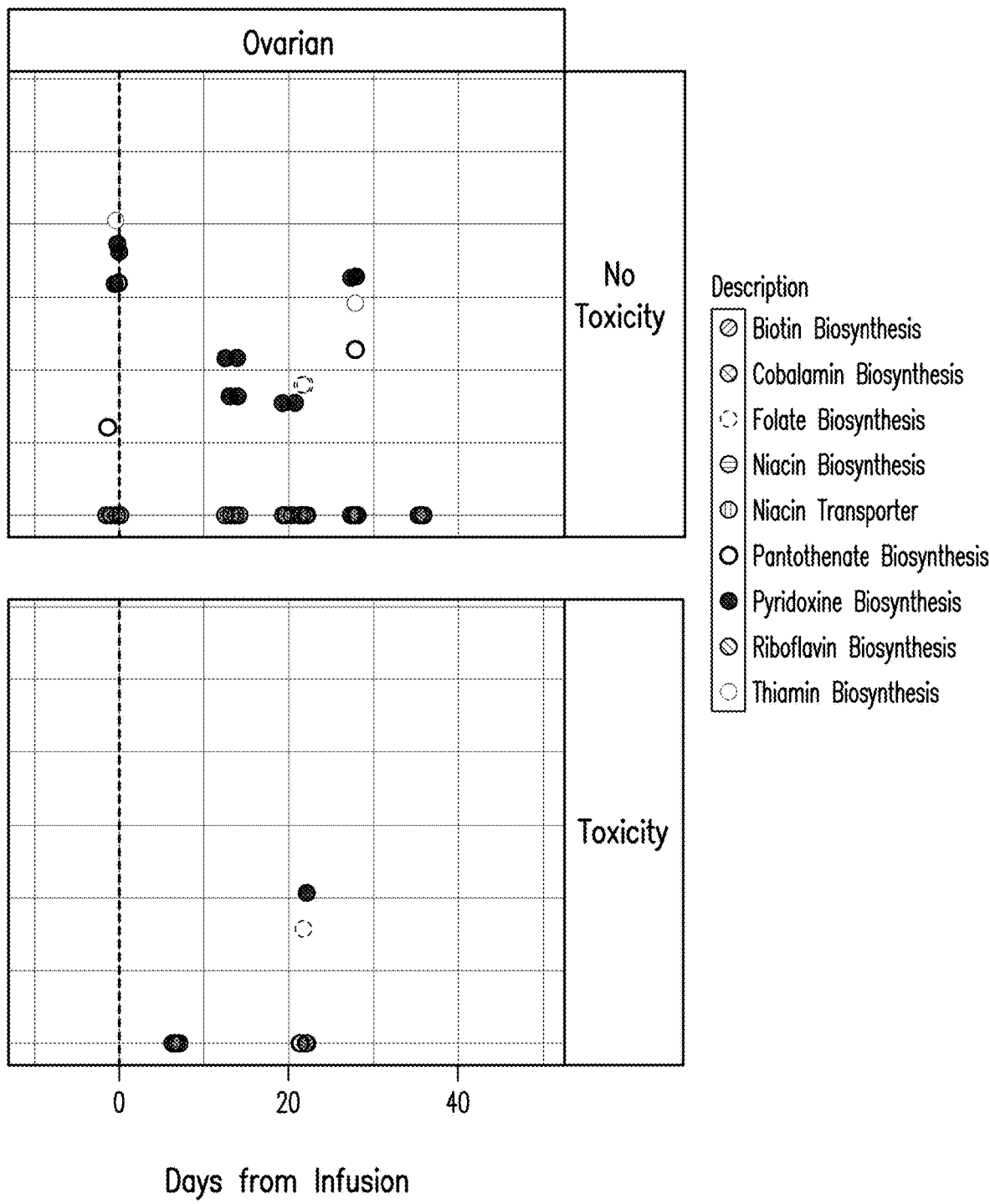

FIG. 9 provides a graph showing relative abundance of bacterial genes associated with biosynthesis of various B vitamins in patients with different types of cancer who exhibited toxicity or did not exhibit toxicity in response to CAR T cell therapy.

Figure 10:
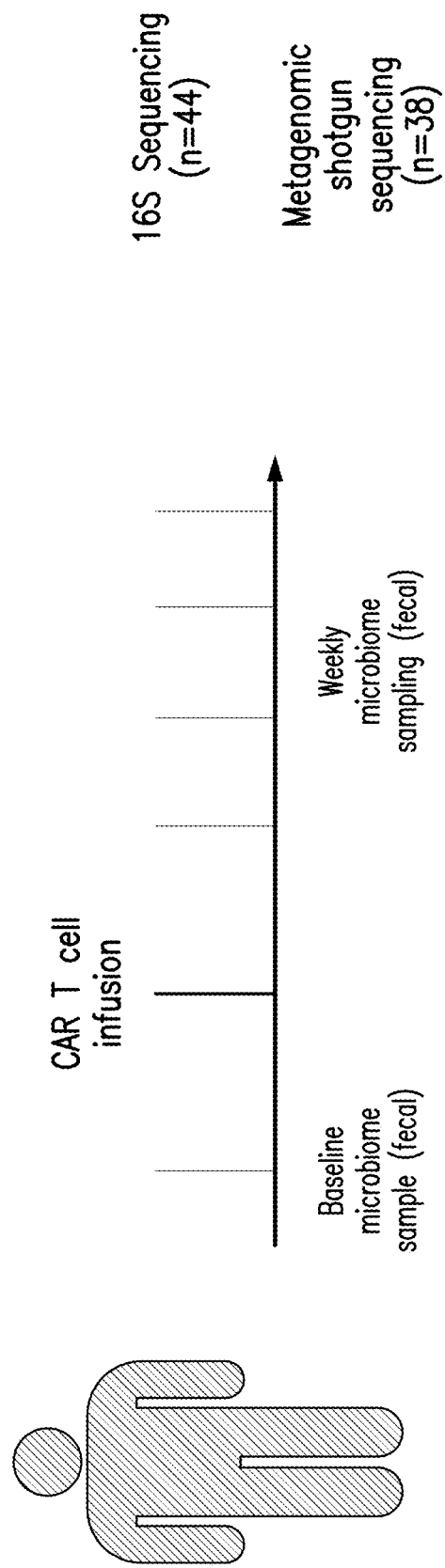

FIG. 10 is a schematic showing of the study design of sample collection and data analysis.

FIG. 11 provides a table showing patients' characteristics.

FIG. 12 provides a table showing the clinical outcome of the recruited patients.

Figure 13A:
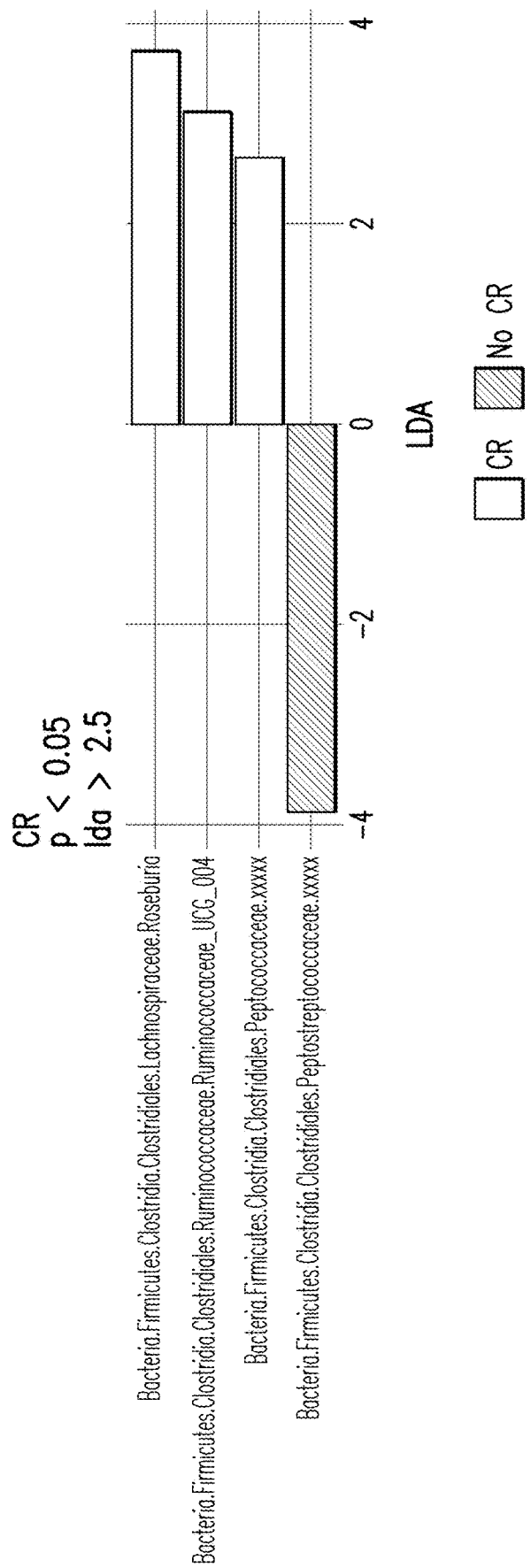
Figure 13B:
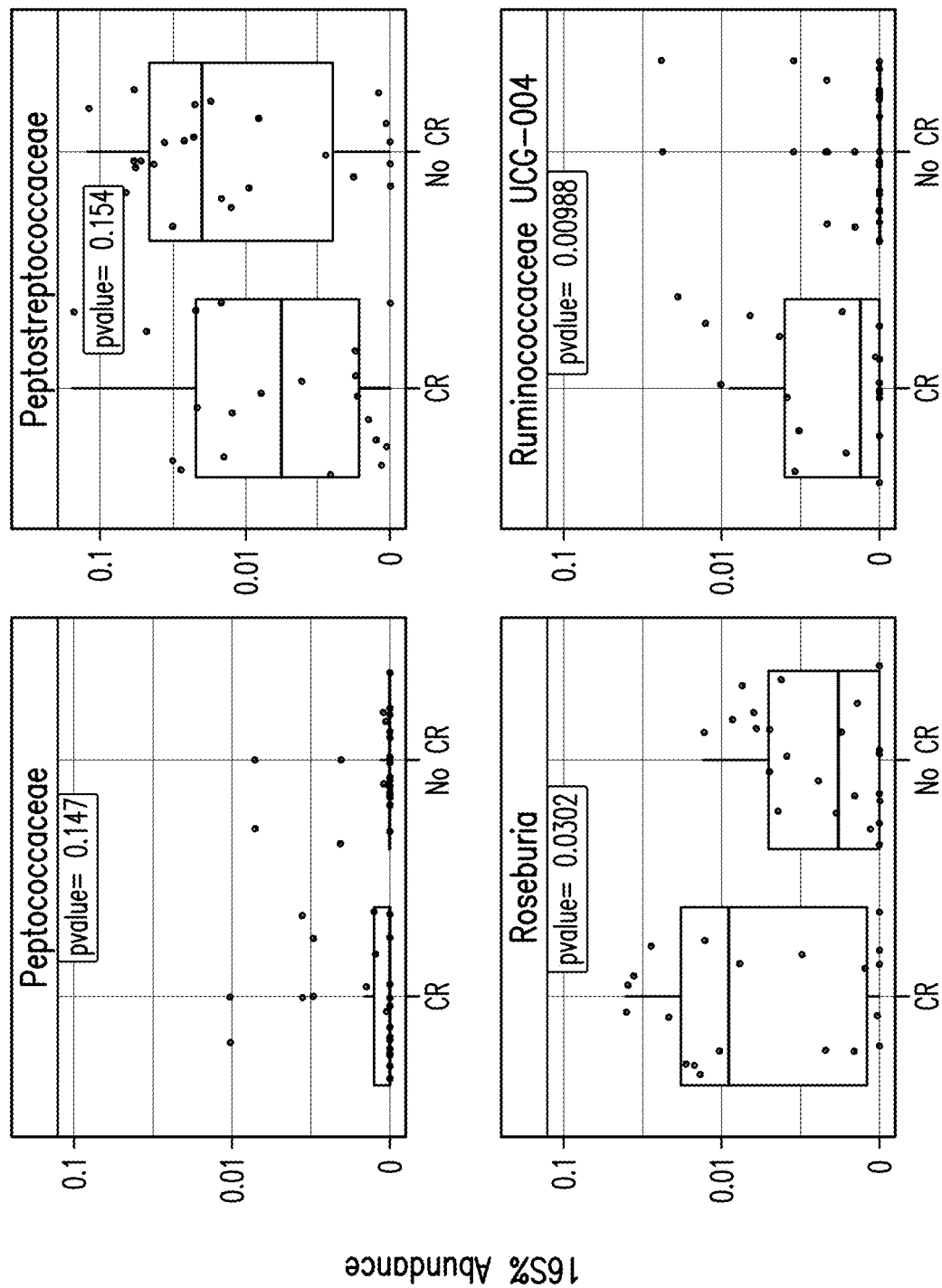

FIGS. 13A-13B provides bacterial taxa associated with complete response following CD19 CAR T cell therapy. (FIG. 13A) LeFSe analysis identified differential bacterial taxa that were associated with complete response (CR) and lack of complete response (No CR). LeFSe assessed all of levels of the bacterial taxa down to the genus level to identify the bacteria that are most associated with the clinical outcome. Taxa were identified with the Silva Database. (FIG. 13B) Bacteria were identified with LeFSe and their association with CR and No CR. 0, not associated with complete response. 1, strongly associated with complete response. P-values were computed with Kruskal Wallis.

5. DETAILED DESCRIPTION

The present invention relates to compositions and methods for identifying patients considered for or undergoing a chimeric antigen receptor (CAR) T cell therapy who are at higher risk for poor response to the CAR T cell therapy or who are likely to achieve a partial or complete response by analyzing the intestinal microbiome of those patients before or during the CAR T cell therapy, and related therapeutic compositions and methods to reduce the risk of poor response and improve the likelihood of partial or complete response to the CAR T cell therapy.

In a CAR T cell therapy, a patient's own T cells are harvested, then genetically modified outside of the patient's body so that the T cells begin to express a chimeric antigen receptor on their surface. The CAR targets cancer cells in the patient's body. After modification, the T cells are then injected back into the patient, where they proceed to recognize the cancer cells and cause an immune response to the cancer cells. The cancer cells are destroyed by the immune response, treating the cancer.

The presently disclosed invention is based in part on the discovery that certain intestinal microbial modules are predictive of a poor response to a CAR T cell therapy, and that certain intestinal microbial modules are predictive of a strong or a complete response to the CAR T cell therapy. The discovery is based on experiments, including those in the Examples disclosed herein, in which the intestinal microbiota of patients were characterized and compared prior to and after a CAR T cell therapy, and their relationship with the patients' response to the CAR T cell therapy.

In certain embodiments, microbiota of the Peptostreptococcaceae family, such as the *Romboutsia* genus, particularly *Romboutsia ileitis*, the Bacteroidaceae family, particularly *Bacteroides uniformis*, or the Clostridiaceae family, particularly *Clostridium butyricum* are predictive of a poor response to a CAR T cell therapy.

In certain embodiments, microbiota of the Lachnospiraceae family, such as members of the *Roseburia* genus, members of the *Pseudobutyrivibrio* genus, particularly *Pseudobutyrivibrio ruminis*, or members of the *Lachnospira* genus, particularly *Lachnospira pectinoschiza*, or particularly or *Clostridium amygdalinum, Clostridium saccharolyticum*, or *Coprococcus comes*, the Rikenellaceae family, particularly *Alistipes indistinctus*, the Lactobacillaceae family, such as the *Lactobacillus* genus, particularly *Lactobacillus fermentum* or *Lactobacillus rogosae*, the Oscillospiraceae family, particularly *Oscillibacter valericigenes*, and the Ruminococcaceae family, such as members of Ruminococcaceae UCG-004 genus, members of the *Anaerotruncus* genus, particularly *Anaerotruncus colihominis*, or particularly *Clostridium methylpentosum*, or the Acidaminococcaceae family, such as members of the *Phascolarctobacterium* genus, particularly *Phascolarctobacterium faecium*, bacteria of the Peptococcaceae family are predictive of a strong or complete response to a CAR T cell therapy.

In particular, microbiota of the Lachnospiraceae family were found in abundance in patients who achieved a strong or complete response to a CAR T cell therapy, while microbiota of the Peptostreptococcaceae family were found in abundance in patients who exhibited a poor response to a CAR T cell therapy.

In addition, a higher than normal abundance of genes associated with B vitamin biosynthesis and genes associated with secondary bile acid biosynthesis and degradation was observed in the intestinal microbiome of patients with a poor response to a CAR T cell therapy, or who were unable to achieve a complete response. In particular a higher than normal abundance of genes for thiamine biosynthesis (e.g., thiH), pantothenic acid biosynthesis (e.g., panC), and pyroxidine biosynthesis (e.g., pdxJ, gapA, dxs) was observed in the intestinal microbiome of patients with poor response to the CAR T cell therapy, or who were unable to achieve a complete response.

For clarity of description, and not by way of limitation, this section is divided into the following subsections:
  5.1 Methods of Predicting Responsiveness to a CAR T cell therapy;
  5.2 Therapeutic bacteria;
  5.3 Pharmaceutical compositions;
  5.4 Methods of Treatment; and
  5.5 Kits.

The following are terms relevant to the present invention:

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

An "individual" or "subject" or "patient" herein is a vertebrate, such as a human or non-human animal, for example, a mammal. Mammals include, but are not limited to, humans, primates, farm animals, sport animals, rodents and pets. Non-limiting examples of non-human animal subjects include birds, such a poultry, including chickens, turkeys, ducks, and geese; rodents such as mice, rats, hamsters, and guinea pigs; rabbits; dogs; cats; sheep; pigs; goats; cattle; horses; and non-human primates such as apes and monkeys.

In certain embodiments, the level or the abundance of a bacterium can be determined by quantification of bacterial DNA or RNA in the sample. In certain embodiments, the bacterial DNA or RNA comprises 16s rDNA or RNA encoded by a bacterial gene unique to the bacterial species. In certain embodiments, the bacterial DNA (e.g., 16s rDNA) or RNA level is determined by a sequencing method, e.g., metagenomic sequencing or shotgun metagenomic sequencing. In certain embodiments, the sequencing is performed using a Illumina MiSeq platform or Illumina HiSeq 2000 platform. In certain embodiments, the bacterial DNA or RNA level (e.g., copy number) is determined by an amplification-based method, e.g., by polymerase chain reaction (PCR), including reverse transcription-polymerase chain reaction (RT-PCR) for RNA quantitative analysis. In certain embodiments, amplification of the bacterial DNA or RNA in a sample may be accomplished by any known method, including but not limited to ligase chain reaction (LCR), transcription-mediated amplification, and self-sustained sequence replication or nucleic acid sequence-based amplification (NASBA). In certain embodiments, the level of a bacterial DNA or RNA level can be determined by size fractionation (e.g., gel electrophoresis), whether or not proceeded by an amplification step. In certain embodiments, the level of a bacterial DNA or RNA level can be determined by sequence-specific probe hybridization. In certain embodiments, the level of a bacterial DNA or RNA level can be determined by mass spectroscopy, PCR, microarray hybridization, thermal sequencing, capillary array sequencing, or solid phase sequencing.

In certain embodiments, the level or the abundance of the bacterium is determined by quantification of one or more proteins unique to the bacteria. In certain embodiments, the protein that is indicative of a bacterium's identity, can be detected but not limited using Western Blot, microarray, gel electrophoresis (such as 2-dimensional gelelectrophoresis), and immunohistochemical assays.

In certain embodiments, the level or the abundance of the bacterium refers to a relative abundance of the bacterium in a sample. The relative abundance of a bacterium refers to the proportion occupied by the particular bacterium in the whole bacterial flora in the sample. The relative abundance of a bacterium can be determined from, for example, the total number of bacterial cells constituting the bacterial flora and the number of the particular bacterial cells included in the bacterial flora. More specifically, for example, genes having a nucleotide sequence that is common in the bacteria included in the bacterial flora and nucleotide sequences characteristic to each bacterial species (for example, 16S rRNA gene) are comprehensively decoded, and the relative abundance of a particular bacterium can be determined by designating the total number of decoded genes and the total number of genes belonging to particular bacterial species as the total number of bacterial cells constituting the bacterial flora and the number of particular bacterial cells, respectively.

In certain embodiments, the level of a bacterial gene is determined by measuring a level of a bacterial nucleic acids include DNA and RNA including at least a portion of the bacterial gene, a bacterial mRNA or cDNA that is transcribed from the bacterial gene, or a sequence complementary or homologous thereto (including but not limited to antisense or small interfering RNA). Said nucleic acid may be included of natural nucleotides and may optionally include nucleotide bases which are not naturally occurring. In certain embodiments, the level of a bacterial gene is determined by measuring a level of a bacterial protein that is encoded by the bacterial gene.

Any suitable methods known in the art for measuring nucleic acid and protein levels can be used with the presently disclosed methods. In certain embodiments, methods for measuring nucleic acid levels include, but not limited to, real-time PCR (RT-PCR), quantitative PCR, quantitative real-time polymerase chain reaction (qRT-PCR), fluorescent PCR, RT-MSP (RT methylation specific polymerase chain reaction), PicoGreen™ (Molecular Probes, Eugene, OR) detection of DNA, radioimmunoassay or direct radio-labeling of DNA, in situ hybridization visualization, fluorescent in situ hybridization (FISH), microarray, sequencing.

In certain embodiments, methods for measuring protein levels include, but are not limited to, mass spectrometry techniques, 1-D or 2-D gel-based analysis systems, chromatography, enzyme linked immunosorbent assays (ELISAs), radioimmunoassays (RIA), enzyme immunoassays (EIA), Western Blotting, immunoprecipitation and immunohistochemistry.

In certain non-limiting embodiments, the subject suffers from a cancer. In certain non-limiting embodiments, the subject is receiving or can receive CAR T cell therapy.

"CART cell therapy" is the killing of cancer cells using a T cell genetically modified to express a chimeric antigen receptor (CAR) that binds to the cancer cells, resulting in activation of the patient's immune system to kill the cancer cells. CAR T cell therapy can be particularly useful in treating acute lymphoblastic leukemia (ALL), non-Hodgkin lymphoma, CD19 malignancies, myeloma other B cell-related or hematologic malignancies, or in treating solid tumors, such as ovarian cancer.

As used herein, a "response to a CAR T cell therapy" refers to a complete response or a partial response to the CAR T cell therapy. A "complete response" or "complete remission" is defined for any given cancer type as the absence of cancer cells detectable by imaging or molecular methods conventionally used for detection of that type of cancer. A "complete response" does not necessarily mean that all cancer cells are absent from the patient. For cancers in which multiple conventional imaging or molecular methods are conventionally used for detection, the absence of detectable cancer cells using any one of such multiple methods is sufficient to indicate a "complete response" for purposes of the present specification. A "partial response" or "partial remission" is defined for any given cancer type as at least a 50% reduction in estimated number of cancer cells or tumor burden detectable by imaging or molecular methods conventionally used for detection of that type of cancer. For cancers in which multiple conventional imaging or molecular methods are conventionally used for detection, a 50% reduction of detectable cancer cells using any one of such multiple methods is sufficient to indicate a "partial response" for purposes of the present specification.

A "poor response" is any response to a CAR T treatment that is not a "complete response" or a "partial response." A poor response can include an increase in cancer cells or tumor burden as detectable using conventional imaging or molecular methods for detection of that type of cancer. A poor response can also include a minimal decrease in cancer cells that is still not sufficient to be considered "partial remission."

"CAR T toxicity" is an early response to CAR T cell therapy and includes cytokine release syndrome and neurotoxicity. Although CAR T toxicity is often considered an adverse reaction, it results from T cell activity and, thus, is also an indicator of likely efficacy of the CAR T cell therapy.

"Cytokine release syndrome" or "CRS" is characterized by high fever, myalgias, malaise, respiratory insufficiency, hemodynamic instability and capillary leak with hypotension, tachycardia, hypoxia, tachypnea, hemophagocytic lymphohistiocytosis/macrophage activation syndrome, or other organ toxicity associated with elevated serum cytokine concentrations. Elevated cytokines and associated molecules include interferon (IFN)-γ, IL-2, soluble IL-2Rα, IL-6, soluble IL-6R, granulocyte-macrophage colony-stimulating factor (GM-CSF), and other cytokines primarily secreted by the monocytes and/or macrophages such as IL-1, IL-6, IL-8, IL-10, IL-12, tumor necrosis factor (TNF)-α, IFN-α, monocyte chemotactic protein (MCP)-1, macrophage inflammatory protein (MIP) la. CRS usually occurs within a few days of administration of the genetically modified T cells to the patient.

"Neurotoxicity" associated with CAR T cell therapy is characterized by encephalopathy, headache, delirium, anxiety, tremor, aphasia, decreased level of consciousness, confusion, seizures, or cerebral edema. Neurotoxicity can be associated with elevated serum concentrations of IL-6, IFN-γ, and TNF-α.

An "effective amount" of a substance as that term is used herein is that amount sufficient to effect beneficial or desired results, including clinical results, and, as such, an "effective amount" depends upon the context in which it is being applied. In the context of administering a composition to reduce the risk of a poor response to CAR T cell therapy or to increase the chance of a complete response or partial response to CAR T cell therapy, an effective amount of a composition described herein is an amount sufficient to decrease the likelihood of a poor response or to increase the likelihood of a complete response or partial response by at 10%, 20%, 30%, 40%, 50%, 60%, 70%, 80%, 90%, 95%, 98% or 99%.

As used herein, and as well-understood in the art, "treatment" or administration of a "therapeutic agent" is an approach for obtaining beneficial or desired results, including clinical results. For purposes of this subject matter, beneficial or desired clinical results include, but are not limited to decreased risk of a poor response to CAR T cell therapy, increased likelihood of a complete response or partial response to CAR T cell therapy, or a combination thereof.

A "probiotic" is a microorganism or group of microorganisms that provides health benefits, or that is non-pathogenic, to a subject when consumed, ingested, or otherwise administered to a subject, for example, a reduction in the likelihood of relapse following cancer treatment. As used herein, the term probiotic can be used to describe, for example, probiotic bacteria and can include the bacteria described herein as well as other bacteria.

A "prebiotic" is a substance that promotes the growth, proliferation and/or survival of one or more bacteria or yeast. As used herein, the term prebiotic can be used to describe, for example, a nutritional supplement including plant fiber, or one or more of poorly-absorbed complex carbohydrates, oligosaccharides, inulin-type fructans or arabinoxylans.

A "postbiotic" is a substance derived from a probiotic organism. As used herein, the term postbiotic can be used to describe, for example, a protein expressed by one or more bacteria, a metabolic product of one or more bacteria, or media from a culture of one or more strains of bacteria.

5.1 Methods of Predicting Responsiveness to a CAR T Cell Therapy

The present disclosure provides methods of identifying a subject as likely to have a response to a CAR T cell therapy. In certain embodiments, the response is a complete response or a partial response. The present disclosure also provides methods of identifying a subject as likely to have no response or a poor response to a CAR T cell therapy.

In certain embodiments, the methods disclosed herein comprise determining the level of a bacterium or spores thereof in a sample from the subject, comparing the level of the bacterium or spores thereof to a reference level, identifying the subject as likely to have a response to the CAR T cell therapy based on the comparison, or identifying the subject as likely to have no response or a poor response to the CAR T cell therapy based on the comparison. In certain embodiments, the methods comprise determining the level of a bacterial gene in a sample from the subject, comparing the level of the bacterial gene to a reference level, identifying the subject as likely to have a response to the CAR T cell therapy based on the comparison, or identifying the subject as likely to have no response or a poor response to the CAR T cell therapy based on the comparison. In certain embodiments, the methods further comprise treating the subject that is identify as likely to have a response to the CAR T cell therapy with the CAR T cell therapy. In certain embodiments, the methods further comprise treating the subject that is identify as likely to have no response or have a poor response to the CAR T cell therapy with the presently disclosed therapeutic bacteria or the pharmaceutical compositions (e.g., as disclosed in the Sections 5.2 and 5.3).

The present disclosure further provides methods of identifying a subject as likely to have a CAR-T cell associated toxicity. In certain embodiments, the CAR-T cell associated toxicity is a cytokine release syndrome or a neurotoxicity. In certain embodiments, the methods comprise determining the level of a bacterium or spores thereof in a sample from the subject, comparing the level of the bacterium or spores thereof to a reference level, identifying the subject as likely to have a CAR-T cell associated toxicity based on the comparison. In certain embodiments, the methods comprise determining the level of a bacterial gene in a sample from the subject, comparing the level of the bacterial gene to a reference level, identifying the subject as likely to have a CAR-T cell associated toxicity based on the comparison. In certain embodiments, the methods further comprise treating the CAR-T cell associated toxicity in the subject.

An increased or decreased level of the bacterium or spores thereof or of the bacterial gene is determined with respect to a reference bacterium or spores thereof level or a reference bacterial gene level. In certain embodiments, the level (e.g., the measured level and the reference level) can be based on a relative abundance in the intestinal microbiome. For instance, the level can represent a percentage of the bacterium or spores thereof of all the bacteria or spores thereof in the intestinal microbiome. The level can also be an absolute number.

In certain embodiments, the reference level is a predetermined level of a bacterium or spores thereof or of a bacterial genetic module that a level higher or lower than the reference level indicates the subject is likely to have a response to the CAR T cell therapy, or is likely to have no response or a poor response to the CAR T cell therapy. In certain embodiments, the reference level is the level of a bacterium or spores thereof or of a bacterial gene from a subject or a population of subjects that have a response to the CAR T cell therapy. In certain embodiments, the reference level is the level of a bacterium or spores thereof or of a bacterial gene from a population of subjects that are candidates for a CAR T cell therapy or subjects with cancer that have not received a CAR T cell therapy. In certain embodiments, the reference level is the level of a bacterium or spores thereof or of a bacterial gene from a sample of the same subject collected at an earlier time point. In certain embodiments, the reference level can be based on a prior test in the same patient, or on levels found in a patient population, such as patients who are candidates for CAR T cell therapy or patients with cancer who have not undergone CAR T cell therapy.

In certain embodiments, the bacterium determined in the sample of the subject is selected from the group consisting of bacteria of the Peptostreptococcaceae family (e.g., the *Romboutsia* genus, e.g., *Romboutsia ileitis*), bacteria of the Bacteroidaceae family (e.g., *Bacteroides uniformis*), bacteria of the Clostridiaceae family (e.g., *Clostridium butyricum, Clostridium saccharolyticum, Clostridium amygdalinum*), bacteria of the Lachnospiraceae family (e.g., the *Roseburia* genus, the *Pseudobutyrivibrio* genus, e.g., *Pseudobutyrivibrio* ruminis, e.g., the *Lachnospira* genus, e.g., *Lachnospira pectinoschiza, Coprococcus comes*), bacteria of the Rikenellaceae family (e.g., *Alistipes indistinctus*), bacteria of the Lactobacillaceae family (e.g., *Lactobacillus* genus, particularly *Lactobacillus fermentum* or *Lactobacillus rogosae*), bacteria of the Oscillospiraceae family (e.g., *Oscillibacter valericigenes*), bacteria of the Ruminococcaceae family (e.g., the Ruminococcaceae UCG-004 genus, the *Anaerotruncus* genus, e.g., *Anaerotruncus colihominis, Clostridium methylpentosum*), bacteria of the Acidaminococcaceae family (e.g., the *Phascolarctobacterium* genus, e.g., *Phascolarctobacterium faecium*), bacteria of the Peptococcaceae family and any combinations thereof.

In certain embodiments, the bacterial gene determined in the sample of the subject is selected from the group consisting of the genes involved in B vitamin biosynthesis (e.g., riboflavin (B2), pantothenate (B5) and thiamine (B1), genes involved in secondary bile acid biosynthesis and degradation, and any combinations thereof. In certain embodiments, the genes involved in B vitamin biosynthesis include thiH, panC, pdxJ, gapA, dxs, and a combination thereof. In certain embodiments, the genes involved in secondary bile acid biosynthesis and degradation include baiA1, baiF, baiE, baiCD, or a combination thereof.

In certain embodiments, the methods disclosed herein further comprise identifying the subject as likely to have a response to the CAR T cell therapy, or as likely to have a CAR T cell associated toxicity, if the level of the bacterium or spores thereof is lower than the reference bacterium or spores thereof level, wherein the bacterium is selected from the group consisting of bacteria of the Peptostreptococcaceae family (e.g., the *Romboutsia* genus, e.g., *Romboutsia ileitis*), bacteria of the Bacteroidaceae family (e.g., *Bacteroides uniformis*), bacteria of the Clostridiaceae family (e.g., *Clostridium butyricum*), and any combinations thereof.

In certain embodiments, the methods disclosed herein further comprise identifying the subject as likely to have a response to the CAR T cell therapy, or as likely to have a CAR T cell associated toxicity, if the level of the bacterium or spores thereof is higher than the reference bacterium or spores thereof level, wherein the bacterium is selected from the group consisting of bacteria of the Lachnospiraceae family (e.g., the *Roseburia* genus, the *Pseudobutyrivibrio* genus, e.g., *Pseudobutyrivibrio ruminis*, e.g., the *Lachnospira* genus, e.g., *Lachnospira pectinoschiza*, e.g., *Coprococcus comes*), bacteria of the Rikenellaceae family (e.g., *Alistipes indistinctus*), bacteria of the Lactobacillaceae family (e.g., the *Lactobacillus* genus, e.g., *Lactobacillus fermentum* or *Lactobacillus rogosae*), bacteria of the Oscillospiraceae family (e.g., *Oscillibacter valericigenes*), bacteria of the Ruminococcaceae family (e.g., the Ruminococcaceae UCG-004 genus, the *Anaerotruncus* genus, e.g., *Anaerotruncus colihominis, Clostridium methylpentosum*), bacteria of the Acidaminococcaceae family (e.g., the *Phascolarctobacterium* genus, e.g., *Phascolarctobacterium faecium*), bacteria of the Clostridiaceae family (e.g., *Clostridium amygdalinum, Clostridium saccharolyticum*), bacteria of the Peptococcaceae family and any combinations thereof.

In certain embodiments, the methods disclosed herein further comprise identifying the subject as likely to have a response to the CAR T cell therapy, or as likely to have a CAR T cell associated toxicity, if the level of the bacterial gene is lower than the reference bacterial gene level, wherein the gene is selected from the group consisting of the genes involved in B vitamin biosynthesis (e.g., riboflavin (B2), pantothenate (B5) and thiamine (B1), genes involved in secondary bile acid biosynthesis and degradation, and any combinations thereof. In certain embodiments, the genes involved in B vitamin biosynthesis include thiH, panC, pdxJ, gapA, dxs, or a combination thereof. In certain embodiments, the genes involved in secondary bile acid biosynthesis and degradation include baiA1, baiF, baiE, baiCD, or a combination thereof.

In certain embodiments, the methods disclosed herein further comprise identifying the subject as likely to have no response or a poor response the CAR T cell therapy, if the level of the bacterium or spores thereof is higher than the reference bacterium or spores thereof level, wherein the bacterium is selected from the group consisting of bacteria of the Peptostreptococcaceae family (e.g., the *Romboutsia* genus, e.g., *Romboutsia ileitis*), bacteria of the Bacteroidaceae family (e.g., *Bacteroides uniformis*), bacteria of the Clostridiaceae family (e.g., *Clostridium butyricum*), and combinations thereof.

In certain embodiments, the methods disclosed herein further comprise identifying the subject as likely to have no response or a poor response the CAR T cell therapy, if the level of the bacterium or spores thereof is lower than the reference bacterium or spores thereof level, wherein the bacterium is selected from the group consisting of bacteria of the Lachnospiraceae family (e.g., the *Roseburia* genus, the *Pseudobutyrivibrio* genus, e.g., *Pseudobutyrivibrio ruminis*, e.g., the *Lachnospira* genus, e.g., *Lachnospira pectinoschiza*, e.g., *Coprococcus comes*), bacteria of the Rikenellaceae family (e.g., *Alistipes indistinctus*), bacteria of the Lactobacillaceae family (e.g., the *Lactobacillus* genus, e.g., *Lactobacillus fermentum* or *Lactobacillus rogosae*), bacteria of the Oscillospiraceae family (e.g., *Oscillibacter valericigenes*), bacteria of the Ruminococcaceae family (e.g., the Ruminococcaceae UCG-004 genus, the *Anaerotruncus* genus, e.g., *Anaerotruncus colihominis, Clostridium methylpentosum*), bacteria of the Acidaminococcaceae family (e.g., the *Phascolarctobacterium* genus, e.g., *Phascolarctobacterium faecium*), bacteria of the Clostridiaceae family (e.g., *Clostridium amygdalinum, Clostridium saccharolyticum*), bacteria of the Peptococcaceae family and any combinations thereof.

In certain embodiments, the methods disclosed herein further comprise identifying the subject as likely to have no response or a poor response the CAR T cell therapy, if the level of the bacterial gene is higher than the reference bacterial gene level, wherein the gene is selected from the group consisting of the genes involved in B vitamin biosynthesis (e.g., riboflavin (B2), pantothenate (B5) and thiamine (B1), genes involved in secondary bile acid biosynthesis and degradation, and any combinations thereof. In certain embodiments, the genes involved in B vitamin biosynthesis is selected from the group consisting of thiH, panC, pdxJ, gapA, dxs, and combinations thereof. In certain embodiments, the genes involved in secondary bile acid biosynthesis and degradation include baiA1, baiF, baiE, baiCD, or a combination thereof.

The sample from the subject can be a fecal sample or an intestinal content sample, for example, a rectal swab.

In certain embodiments, the subject has a cancer. In certain embodiments, the cancer is selected from the group consisting of acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer, CD19 malignancies, and other B cell-related or hematologic malignancies. In certain embodiments, the cancer is an ovarian cancer, a multiple myeloma, or a B-cell malignancy (e.g., a B-cell ALL, CLL, or non-Hodgkin lymphoma), and any combinations thereof. In certain embodiments, the subject or the patient is a human.

Any CAR T cell therapy known in the art can be used with the presently disclosed subject matter. In certain embodiments, the CAR T cell therapy comprises a CAR T cell comprising an extracellular binding domain that binds to mucin 16 (MUC16), B-cell maturation antigen (BCMA), CD19, or a combination thereof.

The amount and/or type of bacteria present in a sample can be determined by measuring the amount or presence of bacterial nucleic acid specific for the type of bacteria, such as 16S rRNA.

The amount and/or type of bacteria present in a sample can be determined by shotgun sequencing of bacterial DNA, PCR amplification of specific genes carried by the bacteria, quantitative PCR of transcripts expressed specifically by the bacteria, antibody based methods of bacterial detection, metabolomic detection of bacterial metabolites, proteomic detection of bacterial proteins, and/or by methods of culturing the microbiota sample.

The amount and/or type of bacterial genes present in a sample can be determined by PCR amplification of the specific genes or quantitative PCR of transcripts expressed specifically by the bacteria, or by tests for the effects of the expression of such genes, such as degradation of secondary bile acids by the microbiota sample.

In certain embodiments, the subject is a candidate for a CAR T cell therapy and has not received the CAR T cell therapy. In certain embodiments, the subject has previously received a CAR T cell therapy. In certain embodiments, the subject is receiving a CAR T cell therapy.

The microbiota sample can be collected from the patient up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days before cells will be harvested from the patient for modification in CAR T cell therapy, or before modified T cells will be administered to the patient in CAR T cell therapy. The microbiota sample can be collected from the subject after cells are harvested from the patient for CAR T cell therapy, but prior to administration of the modified T cell. The microbiota sample can also be collected from the patient 1, 2, 3, 4, 5, 6, 7, 8, 9, 10, 11, 12, 13, or 14 days after administration of the modified T cells to the patient, or after the patient exhibits a symptom of toxicity.

A patient identified as likely to have a poor response to CAR T cell therapy can receive prophylactically therapeutic bacteria or a pharmaceutical composition as described herein (e.g., Sections 5.2 and 5.3) prior to harvesting of cells for modification, between harvesting cells and administration of genetically modified T cells, or after administration of genetically modified T cells in CAR T cell therapy.

A patient identified as likely to have a CAR T cell associated toxicity can be subject to increased monitoring for signs of severe toxicity, can received prophylactic treatments to decrease the chances or effects of severe toxicity, without unduly hampering the effectiveness of CAR T cell therapy, or a combination thereof.

5.2 Therapeutic Bacteria

The present disclosure provides therapeutic bacteria or spores thereof for treating cancer in combination with a CAR T cell therapy, or improving a subject's responsiveness to a CAR T cell therapy. In certain embodiments, the therapeutic bacteria comprise bacteria of the Lachnospiraceae family (e.g., the *Roseburia* genus, the *Pseudobutyrivibrio* genus, e.g., *Pseudobutyrivibrio ruminis*, e.g., the *Lachnospira* genus, e.g., *Lachnospira pectinoschiza*, e.g., *Coprococcus comes*), bacteria of the Rikenellaceae family (e.g., *Alistipes indistinctus*), bacteria of the Lactobacillaceae family (e.g., the *Lactobacillus* genus, e.g., *Lactobacillus fermentum* or *Lactobacillus rogosae*), bacteria of the Oscillospiraceae family (e.g., *Oscillibacter valericigenes*), bacteria of the Ruminococcaceae family (e.g., the Ruminococcaceae UCG-004 genus, the *Anaerotruncus* genus, e.g., *Anaerotruncus colihominis, Clostridium methylpentosum*), bacteria of the Acidaminococcaceae family (e.g., the *Phascolarctobacterium* genus, e.g., *Phascolarctobacterium faecium*), bacteria of the Clostridiaceae family (e.g., *Clostridium amygdalinum, Clostridium saccharolyticum*), bacteria of the Peptococcaceae family or a combination thereof.

In certain embodiments, the present disclosure provides a composition comprising at least one of the presently disclosed bacteria or spores thereof, or a cluster including at least one of the presently disclosed bacteria.

The presently disclosed therapeutic bacteria can be administered in the vegetative or dormant state, or as spores, or a mixture thereof.

Therapeutic bacteria as described herein, any combinations thereof, or a cluster including any one or more of the therapeutic bacteria, can be administered in the form of purified bacteria or spores or other progenitors thereof, or alternatively can be administered as a constituent in a mixture of types of bacteria, optionally including one or more species or cluster of additional bacteria, for example, probiotic bacteria, a probiotic yeast, prebiotic, postbiotic and/or antibiotic.

The present disclosure provides pharmaceutical compositions, and therapeutic uses thereof, as described herein, including such forms of therapeutic bacteria, a combination thereof, or a cluster including any one or more of the therapeutic bacteria, and optionally including one or more species or cluster of additional bacteria, for example, probiotic bacteria, a probiotic yeast, prebiotic, postbiotic and/or antibiotic.

The presently disclosed bacteria can be administered in the form of a liquid, a suspension, a dried (e.g., lyophilized) powder, a tablet, a capsule, or a suppository, and can be administered orally, nasogastrically, or rectally. The bacteria can be administered in a food product, for example, a yogurt food product. A "food product" can mean a product or composition that is intended for consumption by a human or a non-human animal. Such food products include any food, feed, snack, food supplement, liquid, beverage, treat, toy (chewable and/or consumable toys), meal substitute or meal replacement.

The present disclosure provides a composition including an isolated presently disclosed therapeutic bacteria, a combination of any isolate therapeutic bacteria with one another, or a cluster including any one or more of the isolated therapeutic bacteria. The bacteria can be in a formulation for administration to a patient.

The composition can include one, two, three, four, five, six, seven, eight, nine, ten, eleven, twelve, thirteen, fourteen, fifteen, sixteen, seventeen, eighteen, nineteen, twenty, or more, or between twenty and one hundred distinct species of the presently disclosed therapeutic bacteria.

The present disclosure provides a composition including an isolated therapeutic bacteria, which can be one or more of the therapeutic bacteria described herein, but alternate or additional bacteria can be included in other compositions described herein, for example, bacteria which can be naturally occurring bacteria that are in a cluster with any one or more of therapeutic bacteria.

5.3 Pharmaceutical Compositions

The present disclosure provides for pharmaceutical compositions, and therapeutic uses thereof as described herein, which include a therapeutic composition, as described herein, such as, for example, a therapeutic bacteria, as described herein. Such pharmaceutical compositions can further include at least one other agent, such as a stabilizing compound or additional therapeutic agent, for example, a probiotic, prebiotic, postbiotic, and/or antibiotic, and can be administered in any sterile, biocompatible pharmaceutical carrier, including, but not limited to, saline, buffered saline, dextrose, glycerol, polyethylene glycol, and water. The pharmaceutical composition can be in a liquid or lyophilized or freeze-dried form. In some non-limiting embodiments, a formulation includes a diluent (for example, a buffer such as Tris, citrate, acetate or phosphate buffers) having suitable pH values and ionic strengths, solubilizer such as polysorbate (e.g., Tween®), carriers such as human serum albumin or gelatin. In some cases, a preservative can be included that does not affect viability of the organisms in the pharmaceutical composition. Examples of preservatives include thimerosal, parabens, benzylalconium chloride or benzyl alcohol, antioxidants such as ascorbic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in Remington's Pharmaceutical Sciences, 18th ed. A. R. Gennaro, ed. Mack, Easton, PA (1980).

The therapeutic methods and pharmaceutical compositions of the present disclosure can be used for treating a subject having a cancer, decreasing the risk of a poor response to a CAR T cell therapy, increasing the chance of a partial response or complete response to a CAR T cell therapy, improving a subject's responsiveness to a CAR T cell therapy, or a combination thereof. Such therapeutic bacteria are administered to the patient in a pharmaceutically acceptable carrier. The route of administration eventually chosen will depend upon a number of factors and can be ascertained by one skilled in the art.

The pharmaceutical compositions of the present disclosure can be formulated using pharmaceutically acceptable carriers well known in the art in dosages suitable for oral, nasogastric, or rectal administration. Such carriers enable the pharmaceutical compositions to be formulated as tablets, pills, capsules, liquids, gels, syrups, slurries, suspensions and the like, for oral, rectal or nasal ingestion by a patient to be treated. In some non-limiting embodiments, the formulation includes a capsule or tablet formulated for gastrointestinal delivery, e.g., an enteric coated capsule or pill.

Pharmaceutical compositions suitable for use in the present disclosure can include compositions where the active ingredients are contained in an effective amount to achieve the intended purpose. The amount will vary from one individual to another and will depend upon a number of factors, including the intestinal microbiota of the subject, whether cells for modification have been collected from the patient, whether modified T cells have been administered to the patient, the type and dose of cancer treated by the CART cell therapy, the results of any methods described herein to assess the risk of the patient exhibiting a poor response to the CAR T cell therapy or achieving a partial response to complete response to the CAR T cell therapy, the chances of the patient developing toxicity, including severe toxicity, and the overall physical condition of the patient.

The compositions of the present disclosure can be administered for therapeutic treatments, which can include prophylactic treatments. For example, pharmaceutical compositions of the present disclosure can be administered in an amount sufficient to reduce the risk of a poor response to a CAR T cell therapy, or to increase the chance or a partial response or a complete response to a CAR T cell therapy. As is well known in the medical arts, dosages for any one patient depends upon many factors, including stage of the disease or condition, the severity of the disease or condition, the patient's size, body surface area, age, the particular compound to be administered, sex, time and route of administration, general health, and interaction with other drugs being concurrently administered.

A therapeutic bacteria can be administered to a patient alone, or in combination with one or more other drugs, nucleotide sequences, lifestyle changes, etc. used in combination with a CAR T cell therapy, including those designed to treat or reduce the risk of toxicity, including severe toxicity, and/or in pharmaceutical compositions where it is mixed with excipient(s) or other pharmaceutically acceptable carriers.

Single or multiple administrations of formulations can be given depending on the dosage and frequency as required and tolerated by the patient. The formulations can provide a sufficient quantity of active agent to effectively reduce the risk of a poor response to a CAR T cell therapy or to increase the chance of a partial response or a complete response to a CAR T cell therapy.

5.4 Methods of Treatment and Use of Therapeutic Bacteria

The present disclosure provides methods of treating subjects having cancer. In certain embodiments, the present disclosure provides a method of reducing the risk of a poor response to a CAR T cell therapy. In certain embodiments, the present disclosure provides a method of increasing the chance of a partial response to a CAR T cell therapy. In certain embodiments, the present disclosure provides a method of increasing the chance of a complete response to a CAR T cell therapy. In certain embodiments, the present disclosure provides methods of improving a subject's responsiveness to a CAR T cell therapy. In certain non-limiting embodiments, the methods disclosed herein, include administering to the subject, at least one presently disclosed therapeutic bacteria or spores thereof, or a composition comprising thereof (e.g., therapeutic bacteria and pharmaceutical compositions disclosed in Sections 5.2 and 5.3). In certain embodiments, the methods further comprise administering to the subject a CAR-T cell therapy. In certain embodiments, the therapeutic bacteria or spores thereof, or the composition comprising thereof is administered to the subject prior to or during the CAR-T cell therapy. A single method can achieve any two or all three of the previous outcomes.

Patients in need of such treatment or compositions include patients who are receiving or are being considered for or can receive CAR T cell therapy. Such patients typically include patients with certain cancers. In certain embodiments, the cancer is selected from the group consisting of acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer, CD19 malignancies, and other B cell-related or hematologic malignancies. In certain embodiments, the cancer is an ovarian cancer, a multiple myeloma, or a B-cell malignancy (e.g., a B-cell ALL, CLL, or non-Hodgkin lymphoma), and any combinations thereof. In certain embodiments, the subject or the patient is a human.

Such patients can, in particular, include those identified using methods disclosed herein to have an increased risk of poor response to CAR T cell therapy, a decreased risk of partial response or complete response to CAR T cell therapy, or a combination thereof.

The present disclosure provides for a method of decreasing the risk of a poor response to CAR T cell therapy, increasing the chances of a partial response or complete response to CAR T cell therapy, or a combination thereof, by administering, to a patient in need of such treatment, an effective amount of a probiotic including at least one therapeutic bacteria.

The present disclosure provides for a method of treating checkpoint blockade therapy associated colitis by administering, to a patient in need of such treatment, an effective amount of a prebiotic. The prebiotic can be administered separately from the therapeutic bacteria and can promote the growth, proliferation and/or survival of at least one therapeutic bacteria.

The prebiotic can include one or more agents, for example, a nutritional supplement, that increases growth and survival of at least one therapeutic bacteria. The prebiotic can include one or more of poorly-absorbed complex carbohydrates, oligosaccharides, inulin-type fructans or arabinoxylans.

The present disclosure provides for a method of decreasing the risk of a poor response to CAR T cell therapy, increasing the chances of a partial response or complete response to CAR T cell therapy, or a combination thereof, by administering, to a patient in need of such treatment, an effective amount of a postbiotic. The postbiotic can be administered separately from the therapeutic bacteria.

The present disclosure provides for a method of decreasing the risk of a poor response to CAR T cell therapy, increasing the chances of a partial response or complete response to CAR T cell therapy, or a combination thereof, by including determining the risk of a poor response to CAR T cell therapy, the chances of a partial response or complete response to CAR T cell therapy, or both.

The present disclosure provides the use of any composition described herein, including the use of any therapeutic bacteria described herein for decreasing the risk of a poor response to CAR T cell therapy, increasing the chances of a partial response or complete response to CAR T cell therapy, or a combination thereof in a patient. The use can be further characterized by aspects of the methods described above and elsewhere herein.

5.5 Kits

The presently disclosed subject matter provides for kits for diagnosing a subject receiving or considered for CAR T cell therapy, including determining the risk of a poor response to CAR T cell therapy, chances of a partial response or complete response to CAR T cell therapy, or a combination thereof.

The kit can include an agent for determining whether a sample (e.g., a feces sample or an intestinal content sample) of a subject contains an increased or decreased level of a bacterium or spores thereof, or a bacterial gene as compared to a reference level.

An increased or decreased level of the bacterium or spores thereof or of the bacterial gene is determined with respect to a reference bacterium or spores thereof level or a reference bacterial gene level. In certain embodiments, the level (e.g., the measured level and the reference level) can be based on a relative abundance in the intestinal microbiome. For instance, the level can represent a percentage of the bacterium or spores thereof of all the bacteria or spores thereof in the intestinal microbiome. The level can also be an absolute number.

In certain embodiments, the reference level is a predetermined level of a bacterium or spores thereof or of a bacterial genetic module that a level higher or lower than the reference level indicates the subject is likely to have a response to the CAR T cell therapy, or is likely to have no response or a poor response to the CAR T cell therapy. In certain embodiments, the reference level is the level of a bacterium or spores thereof or of a bacterial gene from a subject or a population of subjects that have a response to the CAR T cell therapy. In certain embodiments, the reference level is the level of a bacterium or spores thereof or of a bacterial gene from a population of subjects that are candidates for a CAR T cell therapy or subjects with cancer that have not received a CAR T cell therapy. In certain embodiments, the reference level is the level of a bacterium or spores thereof or of a bacterial gene from a sample of the same subject collected at an earlier time point. In certain embodiments, the reference level can be based on a prior test in the same patient, or on levels found in a patient population, such as patients who are candidates for CAR T cell therapy or patients with cancer who have not undergone CAR T cell therapy.

In certain embodiments, the bacterium determined in the sample of the subject is selected from the group consisting of bacteria of the Peptostreptococcaceae family (e.g., the *Romboutsia* genus, e.g., *Romboutsia ileitis*), bacteria of the Bacteroidaceae family (e.g., *Bacteroides uniformis*), bacteria of the Clostridiaceae family (e.g., *Clostridium butyricum*, *Clostridium saccharolyticum*, *Clostridium amygdalinum*), bacteria of the Lachnospiraceae family (e.g., the *Roseburia* genus, the *Pseudobutyrivibrio* genus, e.g., *Pseudobutyrivibrio ruminis*, e.g., the *Lachnospira* genus, e.g., *Lachnospira pectinoschiza*, *Coprococcus comes*), bacteria of the Rikenellaceae family (e.g., *Alistipes indistinctus*), bacteria of the Lactobacillaceae family, such as the *Lactobacillus* genus, particularly *Lactobacillus fermentum* or *Lactobacillus rogosae*), bacteria of the Oscillospiraceae family (e.g., *Oscillibacter valericigenes*), bacteria of the Ruminococcaceae family (e.g., the Ruminococcaceae UCG-004 genus, the *Anaerotruncus* genus, e.g., *Anaerotruncus colihominis*, *Clostridium methylpentosum*), bacteria of the Acidaminococcaceae family (e.g., the *Phascolarctobacterium* genus, e.g., *Phascolarctobacterium faecium*), bacteria of the Peptococcaceae family and any combinations thereof.

In certain embodiments, the bacterial gene determined in the sample of the subject is selected from the group consisting of the genes involved in B vitamin biosynthesis (e.g., riboflavin (B2), pantothenate (B5) and thiamine (B1), genes involved in secondary bile acid biosynthesis and degradation, and any combinations thereof. In certain embodiments, the genes involved in B vitamin biosynthesis include thiH, panC, pdxJ, gapA, dxs, and a combination thereof. In certain embodiments, the genes involved in secondary bile acid biosynthesis and degradation include baiA1, baiF, baiE, baiCD, or a combination thereof.

The agent can include nucleic acid primers specific for said bacteria or genes, such as nucleic acid primers are specific for 16S rRNA sequencing.

The presently disclosed subject matter also provides for kits for treating a patient who has received or can receive CAR T cell therapy. Such a kit can include one or more therapeutic bacteria or compositions as described herein (e.g., disclosed in Sections 5.2 and 5.3).

The kit can include instructions for administering the therapeutic bacteria or compositions. The instructions can include information about the use of the therapeutic bacterial or compositions in conjunction with CAR T cell therapy. The instructions can include at least one of the following: description of the therapeutic bacteria or composition; dosage schedule and administration; precautions; warnings; indications; counter-indications; over dosage information; adverse reactions; animal pharmacology; clinical studies; and/or references. The instructions can be printed directly on a container (when present) containing the therapeutic bacteria or composition, or as a label applied to the container, or as a separate sheet, pamphlet, card, or folder supplied in or with the container.

The kit can include both components for diagnosing whether a subject receiving or considered for CAR T cell therapy is at an increased or decreased risk of a poor response, partial response, or complete response, or a combination thereof, and components for treating a patient who has or can receive or can CAR T cell therapy. The kit can include instructions for administering components for treating the patient based upon results obtained using the components for diagnosing the patient.

6 EXAMPLES

The presently disclosed subject matter will be better understood by reference to the following Examples, which are provided as exemplary of aspects of the invention, and not by way of limitation.

Example 6.1: Microbiota and Response to CAR T Cell Therapy

Stool samples were collected from intended recipients of CAR T cell therapy after T cell collection and prior to administration of modified T cells. Patients varied in conditioning regimen, CAR construct, and underlying cancer diagnosis. CAR constructs include those targeting mucin 16 (MUC16), B cell maturation antigen (BCMA), and cluster of differentiation 19 (CD 19). Cancers included CD19 malignancies, myeloma, and ovarian cancer. Representative patients included those with solid tumors and hematologic malignancies. 16S RNA was sequenced from the samples and operational taxonomic units (OTUs) were classified using the sequence data with reference to the National Center for Biotechnology Information (NCBI) Reference Sequence Database.

After administration of T cells in connection with the CAR T cell therapy, patients were assessed for signs of toxicity, complete response, or both. For purposes of these Examples, partial responses were not separately identified; patients were assessed solely for a complete response or lack of a complete response based on computed tomography (CT) scan results in patients with solid tumors and lymphoma, or on bone marrow biopsy results in patients with leukemia. Toxicity was determined using clinical grading to be Grade 1 to 4 CRS or Grade 1 to 4 neurotoxicity.

A graph showing relative 16S RNA abundance for various bacterial families in a representative patient is presented in FIG. 1. For all patients, the composition of the microbiota prior to administration of CAR T cells was diverse, as defined by an inverse Simpson diversity index of greater than 4 (FIG. 2).

LEfSe was used to identify microbiota associated with complete response, lack of complete response, toxicity, or combinations thereof using relative abundances of corresponding 16S RNA with a linear discriminant analysis score threshold of greater than 2.5.

LEfSe analysis of patients who exhibited a complete response or lack of a complete response found increased abundance of certain microbiota correlated with complete response or lack of complete response. A graph presenting these results, with relevant linear discriminant analysis (LDA) scores, is presented in FIG. 3. Bacteria in the Oscillospiraceae, Ruminococcaceae, Lachnospiraceae, Acidaminococcaceae, Rikenellaceae, and Lactobacilaceae families were associated with a complete response, while bacteria in the Peptostreptococceceae family were associated with no complete response.

Toxicity exhibited a correlation with a complete response in the patient population (FIG. 4) and, therefore, was used as an indicator of the tendency to have a complete response to CAR T cell therapy. Toxicity typically occurs within days to one to two weeks of administering genetically modified CAR T cells, and therefore can be a suitable early indicator the response to CAR T cell therapy.

Accordingly LEfSe analysis was also conducted based on whether patients exhibited toxicity. Results are presented in FIG. 5. Bacteria in the Lachnospiraceae and Lactobacillaceae families were associated with toxicity. Bacteria in the Bacteroidaceae, Clostridiaceae, and Peptostreptococcaceae families were associated with no toxicity.

In particular, the data of FIG. 3 and FIG. 5 show that Lachnospiraceae are associated with both a complete response and toxicity, while Peptostreptococcaceae are associated with lack of a complete response and lack of toxicity.

Example 6.2: Gene Expression and Response to CAR T Cell Therapy

Fecal samples from eighteen patients of the patient population in Example 1 were subjected to metagenomic sequencing. thiH is associated with thiamin biosynthesis. Additional fecal samples were collected after administration of genetically modified T cells.

pdxJ, gapA, and dxs are associated with pyridoxine biosynthesis. panC is associated with pantothenate biosynthesis. baiA1 is associated with secondary bile acid biosynthesis. baiF, baiE, and baiCD are associated with secondary bile acid degradation. hdgA, gctA, and gtcB are associated with glutarate biosynthesis. atoA and atoD are associated with acetate biosynthesis.

Results are presented as heatmap data in reads per kilobase per million reads (RPKMs) for patients who exhibited a complete response (CR) or no complete response (noCR) (FIG. 6). Patients who did not exhibit a complete response had an increased abundance of bacterial genes associated with B vitamin biosynthesis, secondary bile acid biosynthesis, and secondary bile acid degradation.

Results are also presented as heatmap data in reads per kilobase per million reads (RPKMs) for patients who exhibited a toxicity or no toxicity (FIG. 7). Patients who did not exhibit toxicity response had an increased abundance of bacterial genes associated with B vitamin biosynthesis, secondary bile acid biosynthesis, and secondary bile acid degradation.

Analysis of the relative abundance of bacterial genes associated with biosynthesis of various B vitamins in patients with CD19 malignancies (CD19+ group), myeloma, or ovarian cancer who exhibited a complete response or did not exhibit a complete response to CAR T cell therapy (FIG. 8) showed an increased abundance in vitamin B synthesis genes in patients who did not exhibit a complete response. This is particularly true of myeloma and ovarian cancer patients.

Analysis of the relative abundance of bacterial genes associated with biosynthesis of various B vitamins in patients with CD19 malignancies (CD19+ group), myeloma, or ovarian cancer who exhibited toxicity or did not exhibit toxicity in response to CAR T cell therapy (FIG. 9) showed a somewhat increased abundance in vitamin B synthesis genes in patients who did not exhibit toxicity. This is particularly true of ovarian cancer patients.

Example 6.3: Intestinal Microbiome Analyses Identify Biomarkers for Patient Response to CAR T Cell Therapy Forty-four (44) patients receiving chimeric antigen receptor T cell therapy (median 63 years) were selected for the presently disclosed cohort. The primary inclusion criteria were adult patients who received cellular therapy with CAR T cells, and for whom a microbiota stool specimen was obtained prior to cell infusion. Patients varied in terms of conditioning regimen, CAR construct and underlying diagnosis, with diffuse large B cell lymphoma (DLBCL) being the most prevalent in this cohort. Patient characteristics and clinical outcomes were shown in FIG. 11 and FIG. 12.

As shown in FIG. 10, microbiota stool specimens were collected from each patient at baseline prior to CAR T cell infusion and weekly for four weeks following CAR T cells infusions. The four weeks following CAR T cell infusion was relevant as this was the time period during which toxicity, due to cytokine release syndrome (CRS) or immune effector cell-associated neurotoxicity syndrome (ICANS)/neurotoxicity, may occur. BCMA CAR T cells were used for the treatment of multiple myeloma, CD19 CAR T cells were used for the treatment of B cell malignancies, such as B-cell ALL, CLL, and non-Hodgkin lymphoma. A total of 112 samples were collected from 44 patients. Stool samples were aliquoted and frozen for subsequent processing and batch sequencing.

Stool specimens were sequenced using multiple high-throughput techniques. For 16S rRNA sequencing, silica bead-beating were used to disrupt the bacterial cell walls, then the nucleic acids were isolated using phenol-chloroform extraction. Polymerase chain reaction (PCR) was used to amplify the V4-V5 region of the 16S rRNA gene, which was then sequenced using the Illumina MiSeq platform (Jenq R R et al BBMT 2015, Turnbaugh P J et al Nature 2009). 16S data were analyzed using the DADA2 pipeline (Callahan B J et al Nat Methods 2016).

Shotgun metagenomic sequences from 38 of the 44 samples was performed and the sequences were functionally annotated using the shortBRED pipeline. For shotgun metagenomic sequencing, DNA was extracted as described above and then sheared to a target size of 650 bp using a Covaris ultrasonicator. DNA was then prepared for sequencing using the Illumina TruSeq DNA library preparation kit and sequenced using the Illumina HiSeq system targeting ~10-20×10$^6$ reads per sample with 100 bp, paired-end reads. The abundances of genes assigned to three hypothesized immunological relevant pathways (B vitamin synthesis, bile acid biosynthesis, and short-chain fatty acid production) were inspected.

LeFSe (Segata N et al, Genome Biol. 2011) was performed to identify differential bacterial taxa that were associated with CR and no CR. LeFSe assessed all of levels of the bacterial taxa down to the genus level to identify the bacteria that are most associated with the clinical outcome. Taxa were identified with the Silva Database. LEfSe analysis of patients who exhibited a complete response or lack of a complete response found increased abundance of certain microbiota correlated with complete response or lack of complete response. These results, with relevant linear discriminant analysis (LDA) scores, were presented in FIG. 13A and FIG. 13B.

Based on these data, the increased abundance of the genera—*Roseuria* and Ruminococcaceae UCG-004—were strongly associated with complete response to CAR T cell therapy. Members of these genera can be good consortia as supplement to improve the response to the CAR T cell therapy. Peptococcaceae was also associated with complete response. Peptostreptococcaceae was strongly associated with a lack of a complete response.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for treating a subject having a cancer, comprising:
   (i) (a) determining the level of a bacterium or spores thereof in a sample of the subject;
   (b) comparing the level of the bacterium or spores thereof to a reference bacterium or spores thereof level, wherein the reference bacterium or spores thereof level is a level of the bacterium or spores thereof in a patient that had a CAR T cell therapy response;
   (c) identifying the subject as likely to have a response to a CAR T cell therapy, or as likely to have no response or a poor response to the CAR T cell therapy, based on the comparison; and
   (d) administering the CAR T cell therapy to the subject identified as likely to have a response to the CAR T cell therapy, or administering a therapeutic bacterium or spores thereof or a pharmaceutical comprising thereof to the subject identified as likely to have no response or a poor response to the CAR T cell therapy,
   wherein the bacterium is selected from the group consisting of bacteria of the Peptostreptococcaceae family, bacteria of the Bacteroidaceae family, bacteria of the Clostridiaceae family, bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Peptococcaceae family and combinations thereof; and/or
(ii) (a) determining the level of a bacterial gene in a sample of the subject;
(b) comparing the level of the bacterial gene to a reference bacterial gene level, wherein the reference bacterial gene level is a level of the bacterial gene in a patient that had a CAR T cell therapy response;
(c) identifying the subject as likely to have a response to a CAR T cell therapy, or as likely to have no response or a poor response to the CAR T cell therapy, based on the comparison; and
(d) administering the CAR T cell therapy to the subject identified as likely to have a response to the CAR T cell therapy, or administering a therapeutic bacterium or spores thereof or a pharmaceutical comprising thereof to the subject identified as likely to have no response or a poor response to the CAR T cell therapy,
wherein the bacterial gene is selected from the group consisting of genes involved in vitamin B biosynthesis or secondary bile acid biosynthesis or degradation.

2. The method of claim 1, wherein:
(a) (i) the subject is identified as likely to have a response to the CAR T cell therapy, if the level of the bacterium or spores thereof is lower than the reference bacterium or spores thereof level; or
(ii) the subject is identified as likely to have no response or a poor response to the CAR T cell therapy, if the level of the bacterium or spores thereof is higher than the reference bacterium or spores thereof level,
wherein the bacterium is selected from the group consisting of bacteria of the Peptostreptococcaceae family, bacteria of the Bacteroidaceae family, bacteria of the Clostridiaceae family and any combinations thereof; and/or
(b) (i) the subject is identified as likely to have a response to the CAR T cell therapy, if the level of the bacterium or spores thereof is higher than the reference bacterium or spores thereof level; or
(ii) the subject is identified as likely to have no response or a poor response to the CAR T cell therapy, if the level of the bacterium or spores thereof is lower than the reference bacterium or spores thereof level,
wherein the bacterium is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof.

3. The method of claim 1, wherein:
(i) the subject is identified as likely to have a response to the CAR T cell therapy, if the level of the bacterial gene is lower than the reference bacterial gene level; or
(ii) the subject is identified as likely to have no response or a poor response to the CAR T cell therapy, if the level of the bacterial gene is higher than the reference bacterial gene level.

4. A method for treating a subject having a cancer, comprising:
(a) administering a CAR T cell therapy to the subject,
(i) wherein the subject is identified as likely to have a response to a CAR T cell therapy, and the level of a bacterium or spores thereof in a sample of the subject is lower than a reference bacterium or spores thereof level, wherein the bacterium is selected from the group consisting of bacteria of the Peptostreptococcaceae family, bacteria of the Bacteroidaceae family, bacteria of the Clostridiaceae family, and any combinations thereof; and/or
(ii) wherein the subject is identified as likely to have a response to a CAR T cell therapy, and the level of a bacterium or spores thereof in a sample of the subject is higher than a reference bacterium or spores thereof level, wherein the bacterium is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof; and/or
(iii) wherein the subject is identified as likely to have a response to a CAR T cell therapy, and the level of a bacterial gene in a sample of the subject is lower than a reference bacterial gene level, wherein the bacterial gene is selected from the group consisting of genes involved in vitamin B biosynthesis or secondary bile acid biosynthesis or degradation; or
(b) administering a therapeutic bacterium or spores thereof or a pharmaceutical composition comprising thereof to the subject,
(i) wherein the subject is identified as likely to have no response or a poor response to a CAR T cell therapy, and the level of a bacterium or spores thereof in a sample of the subject is higher than a reference bacterium or spores thereof level, wherein the bacterium is selected from the group consisting of bacteria of the Peptostreptococcaceae family, bacteria of the Bacteroidaceae family, bacteria of the Clostridiaceae family, and any combinations thereof;
(ii) wherein the subject is identified as likely to have no response or a poor response to a CAR T cell therapy, and the level of a bacterium or spores thereof in a sample of the subject is lower than a reference bacterium or spores thereof level, wherein the bacterium is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof; and/or
(iii) wherein the subject is identified as likely to have no response or a poor response to a CART cell therapy, and the level of a bacterial gene in a sample of the subject is higher than a reference bacterial gene level, wherein the bacterial gene is selected from the group consisting of genes involved in vitamin B biosynthesis or secondary bile acid biosynthesis or degradation,
wherein the reference bacterium or spores thereof level is a level of the bacterium or spores thereof in a patient that had a CAR T cell therapy response and/or the reference bacterial gene level is a level of the bacterial gene in a patient that had a CAR T cell therapy response.

5. The method of claim 4, wherein:
(a) the bacteria of the Peptostreptococcaceae family comprise bacteria of the *Romboutsia* genus;
(b) the bacteria of the Bacteroidaceae family comprise *Bacteroides uniformis*;
(c) the bacteria of the Clostridiaceae family of (i) comprise *Clostridium butyricum*; and/or
(d) the bacteria of the Clostridiaceae family of (ii) comprise *Clostridium amygdalinum, Clostridium saccharolyticum* or a combination thereof.

6. The method of claim 4, wherein:
(a) the genes involved in vitamin B biosynthesis include thiH, panC, pdxJ, gapA, dxs or a combination thereof; and/or
(b) the genes involved in secondary bile acid biosynthesis and degradation include baiA1, baiF, baiE, baiCD or a combination thereof.

7. The method of claim 4, wherein the sample is a fecal sample or an intestinal content sample of the subject.

8. The method of claim 4, wherein the cancer is an ovarian cancer, a multiple myeloma, a B-cell malignancy, or a combination thereof.

9. The method of claim 4, wherein the CAR T cell therapy comprises a CAR T cell comprising an extracellular binding domain that binds to mucin 16 (MUC16), B-cell maturation antigen (BCMA), CD19 or a combination thereof.

10. The method of claim 4, wherein the therapeutic bacterium or spores is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof.

11. A method for identifying a subject having a cancer as likely to have a response to a CAR T cell therapy, or as likely to have no response or a poor response to the CAR T cell therapy:
(i) (a) determining the level of a bacterium or spores thereof in a sample of the subject;
(b) comparing the level of the bacterium or spores thereof to a reference bacterium or spores thereof level, wherein the reference bacterium or spores thereof level is a level of the bacterium or spores thereof in a patient that had a CAR T cell therapy response;
(c) identifying the subject as likely to have a response to the CAR T cell therapy, or as likely to have no response or a poor response to the CAR T cell therapy, based on the comparison,
wherein the bacterium is selected from the group consisting of bacteria of the Peptostreptococcaceae family, bacteria of the Bacteroidaceae family, bacteria of the Clostridiaceae family, bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Peptococcaceae family and combinations thereof; and/or (ii) (a) determining the level of a bacterial gene in a sample of the subject;
(b) comparing the level of the bacterial gene to a reference bacterial gene level, wherein the reference bacterial gene level is a level of the bacterial gene in a patient that had a CAR T cell therapy response; and
(c) identifying the subject as likely to have a response to the CAR T cell therapy, or as likely to have no response or a poor response to the CAR T cell therapy, based on the comparison;
wherein the bacterial gene is selected from the group consisting of genes involved in vitamin B biosynthesis or secondary bile acid biosynthesis or degradation.

12. The method of claim 11, wherein:
(a) (i) the subject is identified as likely to have a response to the CAR T cell therapy, if the level of the bacterium or spores thereof is lower than the reference bacterium or spores thereof level; or (ii) the subject is identified as likely to have no response or a poor response to the CAR T cell therapy, if the level of the bacterium or spores thereof is higher than the reference bacterium or spores thereof level,
wherein the bacterium is selected from the group consisting of bacteria of the Peptostreptococcaceae family, bacteria of the Bacteroidaceae family, bacteria of the Clostridiaceae family, and any combinations thereof; and/or
(b) (i) the subject is identified as likely to have a response to the CAR T cell therapy, if the level of the bacterium or spores thereof is higher than the reference bacterium or spores thereof level; or (ii) the subject is identified as likely to have no response or a poor response to the CAR T cell therapy, if the level of the bacterium or spores thereof is lower than the reference bacterium or spores thereof level,
wherein the bacterium is selected from the group consisting of bacteria of the Lachnospiraceae family, bacteria of the Rikenellaceae family, bacteria of the Lactobacillaceae family, bacteria of the Oscillospiraceae family, bacteria of the Ruminococcaceae family, bacteria of the Acidaminococcaceae family, bacteria of the Clostridiaceae family, bacteria of the Peptococcaceae family and any combinations thereof.

13. The method of claim 11, wherein:
(i) the subject is identified as likely to have a response to the CAR T cell therapy, if the level of the bacterial gene is lower than the reference bacterial gene level; or
(ii) the subject is identified as likely to have no response or a poor response to the CAR T cell therapy, if the level of the bacterial gene is higher than the reference bacterial gene level.

14. The method of claim 11, wherein the CAR T cell therapy comprises a CAR T cell comprising an extracellular binding domain that binds to mucin 16 (MUC16), B-cell maturation antigen (BCMA), CD19, or a combination thereof.

15. The method of claim 11, wherein the response to the CAR T cell therapy is a partial response or a complete response.

* * * * *